US007422744B2

(12) United States Patent
Huse et al.

(10) Patent No.: US 7,422,744 B2
(45) Date of Patent: Sep. 9, 2008

(54) METHODS OF TREATING CANCER WITH ALPHAVBETA3-SPECIFIC ANTIBODIES

(75) Inventors: William D Huse, Del Mar, CA (US); Scott M Glaser, San Diego, CA (US)

(73) Assignee: Applied Molecular Evolution, Inc., San Diego, CA (US)

( * ) Notice: Subject to any disclaimer, the term of this patent is extended or adjusted under 35 U.S.C. 154(b) by 241 days.

(21) Appl. No.: 10/452,440

(22) Filed: May 30, 2003

(65) Prior Publication Data

US 2003/0208048 A1 Nov. 6, 2003

Related U.S. Application Data

(63) Continuation of application No. 08/791,391, filed on Jan. 30, 1997, now Pat. No. 6,590,079.

(51) Int. Cl.
*A61K 39/395* (2006.01)
*C07K 16/28* (2006.01)

(52) U.S. Cl. ............... 424/144.1; 424/130.1; 424/133.1; 424/141.1; 424/143.1; 424/153.1; 424/154.1; 424/173.1; 530/387.1; 530/387.3; 530/388.1; 530/388.2; 530/388.22; 530/388.73; 530/388.75

(58) Field of Classification Search ....................... None
See application file for complete search history.

(56) References Cited

U.S. PATENT DOCUMENTS

| | | | |
|---|---|---|---|
| 5,225,539 A | 7/1993 | Winter | 530/387.3 |
| 5,264,563 A | 11/1993 | Huse | 536/25.3 |
| 5,523,388 A | 6/1996 | Huse | 536/22.1 |
| 5,578,704 A | 11/1996 | Kim et al. | 530/388.22 |
| 5,585,089 A | 12/1996 | Queen et al. | 424/133.1 |
| 5,693,762 A | 12/1997 | Queen et al. | 530/387.3 |
| 5,753,230 A | 5/1998 | Brooks et al. | 424/158.1 |
| 5,766,591 A * | 6/1998 | Brooks et al. | 424/184.1 |
| 6,096,551 A | 8/2000 | Barbas et al. | 436/6 |
| 6,180,370 B1 | 1/2001 | Queen et al. | 435/69.6 |
| 6,531,580 B1 | 3/2003 | Huse et al. | 530/388.22 |
| 6,590,079 B2 | 7/2003 | Huse et al. | 530/388.22 |
| 6,887,473 B1 * | 5/2005 | Brooks et al. | 424/152.1 |

FOREIGN PATENT DOCUMENTS

| | | |
|---|---|---|
| EP | 0 451 216 B1 | 10/1991 |
| EP | 0 682040 A1 | 11/1995 |
| WO | WO 95/25543 A | 9/1995 |
| WO | WO 96/40250 A | 12/1996 |
| WO | WO 98/33919 | 8/1998 |

OTHER PUBLICATIONS

Webster's II New Riverside University Dictionary, The Riverside Publishing Company, Boston, 1994; p. 385.*
Dorland's Illustrated Medical Dictionary, Twenty-sixth Edition (W.B. Saunders Company, Philadelphia, 1981; p. 385.*
Illustrated Stedman's Medical Dictionary 24th Edition, Williams & Wilkins, Baltimore, 1982; p. 403.*
Adams et al., "Increased Affinity Leads to Improved Selective Tumor Delivery of Single-Chain Fv Antibodies," *Cancer Res.*, 58:485-490 (1998).
Alfthan, *Biosensors and Bioelectronics*, "Surface plasmon resonance biosensors as a tool in antibody engineering," 13:653-663 (1998).
Beidler C., "Mammalian expression and characterization of a dimeric single chain antibody specific for integrin alpha-v-beta-3," *Immunotechnology* vol. 2 p. 297 (1996).
Biotechnology Newswatch, pp. 11-12, Jan. 16, 1995.
Biotechnology Newswatch, pp. 11, Feb. 6, 1995.
Brooks et al., "Integrin -$\alpha v \beta_3$ Antagonists Promote Tumor Regression by Inducing Apoptosis of Angiogenic Blood Vessels," *Cell* 79:1157-1164 (1994).
Carmeliet, P., "Integrin indecision," *Nature Medicine* 8:14-16 (2002).
Cheresh, D.A., "Human endothelial cells synthesize and express an Arg-Gly-Asp-directed adhesion receptor involved n attachment to fibrinogen and von Willebrand factor," *Proc. Natl. Acad. Sci. USA* 84:6471-6475 (1987).
Cheresh and Spiro, "Biosynthetic and Functional Properties of an Arg-Gly-Asp-directed Receptor Involved in Human Melanoma Cell Attachment to Vitronectin, Fibrinogen, and von Willebrand Factor," *J. Biol. Chem.* 262(36):17703-17711 (1987).
Cheresh and Stupack, "Integrin-mediated death: An explanation of the integrin-knockout phenotype," *Nature Medicine* 8:193-194 (2002).
Choi et al., "Inhibition of neointimal hypersplasia by blocking -$\alpha v \beta_3$ integrin with a small peptide antagonist GpenGRGDSPCA," *J. Vascular Surg.*, 19:125-134 (1994).
Chothia et al., "Canonical Structures for the Hypervariable Regions of Immunoglobulins," *J. Mol. Biol.* 196:901-917 (1987).

(Continued)

*Primary Examiner*—Phillip Gambel
(74) *Attorney, Agent, or Firm*—McDermott Will & Emery LLP

(57) ABSTRACT

The invention provides a Vitaxin antibody and a LM609 grafted antibody exhibiting selective binding affinity to $\alpha_v \beta_3$. The Vitaxin antibody consists of at least one Vitaxin heavy chain polypeptide and at least one Vitaxin light chain polypeptide or functional fragments thereof. Also provided are the Vitaxin heavy and light chain polypeptides and functional fragments. The LM609 grafted antibody consists of at least one CDR grafted heavy chain polypeptide and at least one CDR grafted light chain polypeptide or functional fragment thereof. Nucleic acids encoding Vitaxin and LM609 grafted heavy and light chains as well as nucleic acids encoding the parental non-human antibody LM609 are additionally provided. Functional fragments of such encoding nucleic acids are similarly provided. The invention also provides a method of inhibiting a function of $\alpha_v \beta_3$. The method consists of contacting $\alpha_v \beta_3$ with Vitaxin or a LM609 grafted antibody or functional fragments thereof under conditions which allow binding to $\alpha_v \beta_3$. Finally, the invention provides for a method of treating an $\alpha_v \beta_3$-mediated disease. The method consists of administering an effective amount of Vitaxin or a LM609 grafted antibody or functional fragment thereof under conditions which allow binding to $\alpha_v \beta_3$.

34 Claims, 10 Drawing Sheets

OTHER PUBLICATIONS

Chowdhury et al., "Improving antibody affinity by mimicking somatic hypermutation in vitro," *Nature Biotech* 17:568-572 (1999).

Clark, M. (ed.), "Protein Engineering of Antibody Molecules for Prophylactic and Therapeutic Applications in Man," Nottingham, England: Academic Titles (1993).

Davies and Riechmann, "Affinity improvement of single antibody VH domains: residues in all three hypervariable regions affect antigen binding," *Immunotechnology* 2:169-179 (1996).

Day, E.D., *Advanced Immunochemistry*, Second Ed., Wiley-Liss, Inc., New York, NY (1990).

Devlin et al., "Random Peptide Libraries: A Source of Specific Protein Binding Molecules," *Science* 249:404-406, (1990).

Dueñas et al., "selection of phage displayed antibodies based on kinetic constants," *Molec. Immunol.*, 33(3):279-285 (1996).

Foote and Milstein, "Kinetic maturation of an immune response," *Nature* 352:530-532 (1991).

Glaser et al., "Antibody Engineering by Condon-Based Mutagenesis in a Filamentous Phage Vector System," *J. Immunol.* 149:3903-3913 (1992).

Hawkins et al., "Selection of Phage Antibodies by Binding Affinity, Mimicking Affinity Maturation," *J. Mol. Biol.*, 226:889-896 (1992).

Huse, W.D., "Combinatorial Antibody Expression Libraries in Filamentous Phage," In: Antibody Engineering: A Practical Guide, C.A.K. Borrebaeck, ed. W.H. Freeman and Co., Publishers, New York, pp. 103-120 (1991).

Huse et al., "Applications of a Filamentous Phage pVIII Fusion Protein System Suitable for Efficient Production, Screening, and Mutagenesis of F(ab) Antibody Fragments," *J. Immunol.* 149:3914-3920 (1992).

Huston et al., "Antigen Recognition and Targeted Delivery by the Single-Chain Fv," *Cell Biophysics*, 22:189-224 (1993).

Kabat et al., U.S. Dept. of Health and Human Services, "Sequences of Proteins of Immunological Interest," vol. 1 (1991).

MacCallum et al., "Antibody-antigen Interactions: Contact Analysis and Binding Site Topography," *J. Mol. Biol.* 262:732-745 (1996).

Moore et al., "Directed evolution of *para*-nitrobenzyl esterase for aqueous-organic solvents," *Nature Biotechnology* 14:458-467 (1996).

Myszka et al., "Kinetic analysis of a protein-antibody interaction limited by mass transportation on an optical biosensor," *Biophys. Chem.*, 64:127-137 (1997).

Newman et al., ""Primatization" of Recombinant Antibodies for Immunotherapy of Human Diseases: A Macaque/Human Chimeric Antibody Against Human CD4," *Biotechnol.*, 10:1455-1460 (1992).

Padlan, Eduardo A., "A Possible Procedure For Reducing the Immunogenicity of Antibody Variable Domains While Preserving Their Ligand-Binding Properties," *Molecular Immunol.* 28(4/5):489-498 (1991).

Posey et al., "A Pilot Trial of Vitazin, A Humanized Anti-Vitronection Receptor (anti $\alpha v \beta_3$) Antibody in Patients with Metastic Cancer," *Cancer Biotherapy & Radiopharmaceuticals* 16:125-132 (2001).

Plückthun and Skerra, "Expression of functional antibody Fv and Fab fragments in *Escherichia coli*," *Meth. Enzymol.* 178:497-515 (1989).

Rader et al., "A phage display approach for rapid antibody humanization: Designed combinatorial V gene libraries," *Proc. Natl. Acad. Sci. USA*, 95:8910-8915 (1998).

Reynolds et al., "Enhanced pathological angiogenesis in mice lacking $\beta_3$ integrin or $\beta_3$ and $\beta_5$ integrins," *Nature Medicine* 8:27-34 (2002).

Rosok et al., "A Combinatorial Library Strategy for the Rapid Humanization of Anticarcinoma BR96 Fab," *J. Biol. Chem.* 271:22611-22618 (1996).

Sandberg and Terwilliger, "Engineering multiple properties of a protein by combinatorial mutagenesis," *Proc. Natl. Acad. Sci.* 90:8367-8371 (1993).

Schier et al., "Isolation of Picomolar Affinity Anti-c-erbB-2 Single-chain fv by Molecular4 Evolution of the Complimentarity Determining Regions in the Center of the Antibody Binding Site," *J. Mol. Biol.*, 263:551-567 (1996).

Schier et al., "Isolation of High-Affinity Monomeric Human Anti-c-ervB-2 Single-chain Fv Using Affinity-driven Selection," *J. Mol. Biol.*, 255:28-43 (1996).

Schier and Marks, "Efficient in vitro affinity maturation of phage antibodies using BIA core guided selections," *Hum. Antibod. Hybridomas*, 7:97-105 (1996).

Singer et al., "Optimal Humanization of 1B4, an Anti-CD18 Murine Monoclonal Antibody, is Achieved by Correct Choice of Human V-Region Framework Sequences," *J. Immunol.* 150(7):2844-2857 (1993).

Studnicka et al., "Human engineered monoclonal antibodies retain full specific binding activity by preserving non-CDR complimentarity-modulating residues," *Protein Engineering* 7:805-814 (1994).

Stupack and Cheresh, "Get a ligand, get a life: integrins, signaling and cell survival," *J. Cell Sci.* 115:3729-3738 (2002).

Thompson et al., "Affinity Maturation of a High-Affinity Human Monoclonal Antibody Against the Third Hypervariable Loop of Human Immunodeficiency Virus: Use of Phage Display to Improve Affinity and Broaden Strain Reactivity," *J. Mol. Biol.* 256:77-88 (1996).

Wu et al., "Stepwise in vitro affinity maturation of Vitaxin, an -$\alpha v \beta_3$-specific humanized mAb," *Proc. Natl. Acad. Sci. USA*, 95:6037-6042 (1998).

Yelton et al., "Affinity Maturation of the BR96 Anti-Carcinoma Antibody by Condon-Based Mutagenesis," *J. Immunol.* 155:1994-2004 (1995).

* cited by examiner

```
CAG GTG CAG CTG GTG GAG TCT GGG GGA GGC GTT GTG CAG CCT GGA AGG    48
Gln Val Gln Leu Val Glu Ser Gly Gly Gly Val Val Gln Pro Gly Arg
 1           5               10              15

TCC CTG AGA CTC TCC TGT GCA GCC TCT GGA TTC ACC TTC AGT AGC TAT    96
Ser Leu Arg Leu Ser Cys Ala Ala Ser Gly Phe Thr Phe Ser Ser Tyr
             20              25              30

GAC ATG TCT TGG GTT CGC CAG GCT CCG GGC AAG GGT CTG GAG TGG GTC   144
Asp Met Ser Trp Val Arg Gln Ala Pro Gly Lys Gly Leu Glu Trp Val
         35              40              45

GCA AAA GTT AGT GGT GGG AGC ACC AAT GAC TAC TAT TTA GAC ACT GTG   192
Ala Lys Val Ser Gly Gly Ser Thr Asn Asp Tyr Tyr Leu Asp Thr Val
     50              55              60

CTG CAA ATG AAC AGC CTG AGA GCC GAG GAC ACC ATC TTC TAC TGT GCT   240
Leu Gln Met Asn Ser Leu Arg Ala Glu Asp Thr Ile Phe Tyr Cys Ala
         65              70              75              80

AGT TTT GCC GAG GCC ACA GAC AAT AGT AAG AAC ACC CTA TAC TAC TGT   288
Ser Phe Ala Glu Ala Thr Asp Asn Ser Lys Asn Thr Leu Tyr Tyr Cys
             85              90              95

GCA AGA CAT AAC TAC GGC TAC TGG TAC TTT GCT GGG CAA GGG ACT ACA   336
Ala Arg His Asn Tyr Gly Tyr Trp Tyr Phe Ala Gly Gln Gly Thr Thr
            100             105             110

GTG ACT GTT TCT AGT                                                351
Val Thr Val Ser Ser
            115
```

FIG. 1A

```
GAG ATT GTG CTA ACT CAG TCT CCA GCC ACC CTG TCT CTC AGC CCA GGA         48
Glu Ile Val Leu Thr Gln Ser Pro Ala Thr Leu Ser Leu Ser Pro Gly
  1           5              10              15

GAA AGG GCG ACT CTT TCC TGC CAG GCC AGC AGT ATT AGC AAC CAC             96
Glu Arg Ala Thr Leu Ser Cys Gln Ala Ser Ser Ile Ser Asn His
              20              25              30

CTA CAC TGG TAT CAA CAA AAG CCA GGG ATC TCT CCC AGG CTT CTC ATC         144
Leu His Trp Tyr Gln Gln Lys Pro Gly Ile Ser Pro Arg Leu Leu Ile
          35              40              45

AAG TAT CGT TCC CAG TCA GGG GTC CCA GCC AGG TTC AGT GGC AGT GGG         192
Lys Tyr Arg Ser Gln Ser Gly Val Pro Ala Arg Phe Ser Gly Ser Gly
     50              55              60

AGT GGA TCA GGG ACA GAT TTC ACC CTC ACC ATC TCC AGT CTG GAG CCT         240
Ser Gly Ser Gly Thr Asp Phe Thr Leu Thr Ile Ser Ser Leu Glu Pro
 65              70              75              80

GAA GAT TTT GCA GTC TAT TAC TGT CAA CAG TAC AGT AGC TGG CCT CAC         288
Glu Asp Phe Ala Val Tyr Tyr Cys Gln Gln Tyr Ser Ser Trp Pro His
              85              90              95

ACG TTC GGA GGG GGG ACC AAG GTG GAA ATT AAG                             321
Thr Phe Gly Gly Gly Thr Lys Val Glu Ile Lys
         100             105
```

FIG. 1B

```
GAA GTG CAG CTG GTG GAG TCT GGG GGA GGC TTA GTG AAG CCT GGA AGG      48
Glu Val Gln Leu Val Glu Ser Gly Gly Gly Leu Val Lys Pro Gly Arg
 1                   5                  10                  15

TCC CTG AGA CTC TCC TGT GCA GCC TCT GGA TTC AGT AGC TAT           96
Ser Leu Arg Leu Ser Cys Ala Ala Ser Gly Phe Ser Ser Tyr
             20                  25                  30

GAC ATG TCT TGG GTT CGC CAG ATT CCG GAG AAG CTG GAG TGG GTC      144
Asp Met Ser Trp Val Arg Gln Ile Pro Glu Lys Leu Glu Trp Val
         35                  40                  45

GCA AAA GTT AGT GGT GGT AGC ACC TAC TAT TAT GAC ACT GTG          192
Ala Lys Val Ser Gly Gly Ser Thr Tyr Tyr Tyr Asp Thr Val
     50                  55                  60

CAG GGC CGA TTC ACC ATC TCC AGA GAC AAT GCC AAG AAC ACC TAC TAC   240
Gln Gly Arg Phe Thr Ile Ser Arg Asp Asn Ala Lys Asn Thr Tyr
 65                  70                  75                  80

CTG CAA ATG AGC AGT CTG GAG GAC GAC GCC ACA ATG TAT ATG TAC TGT   288
Leu Gln Met Ser Ser Leu Glu Asp Asp Ala Thr Met Tyr Met Tyr Cys
             85                  90                  95

GCA AGA CAT AAC TAC GGC TAC TTT GCT TAC TGG GGC CAA GGG ACT CTG   336
Ala Arg His Asn Tyr Gly Tyr Phe Ala Tyr Trp Gly Gln Gly Thr Leu
        100                 105                 110

GTC ACT GTC TCT GCA                                              351
Val Thr Val Ser Ala
        115
```

FIG. 2A

```
GAT ATT GTG CTA ACT CAG TCT CCA GCC ACC CTG TCT GTG ACA CCA GGA       48
Asp Ile Val Leu Thr Gln Ser Pro Ala Thr Leu Ser Val Thr Pro Gly
 1               5                  10                  15

GAT AGC GTC AGT CTT TCC TGC AGG GCC AGC CAA AGT ATT AGC AAC CAC       96
Asp Ser Val Ser Leu Ser Cys Arg Ala Ser Gln Ser Ile Ser Asn His
                20                  25                  30

CTA CAC TGG TAT CAA CAA CAA AAA TCA CAT GAG TCT CCT CTC ATC           144
Leu His Trp Tyr Gln Gln Gln Lys Ser His Glu Ser Pro Leu Ile
         35                  40                  45

AAG TAT CGT TCC CAG TCT GGG ATC CCC TCC AGG TTC AGT GGC                192
Lys Tyr Arg Ser Gln Ser Gly Ile Pro Ser Arg Phe Ser Gly
 50                  55                  60

AGT GGA TCA ACA GAT TAT TTC GCT CTC AGT AAC AGT GTG GAG ACT           240
Ser Gly Ser Thr Asp Tyr Phe Ala Leu Ser Asn Ser Val Glu Thr
 65                  70                  75                  80

GAA GAT TTT GGA ATG TAT TTC TGT CAA CAG AGT GGC TGG CCT CAC           288
Glu Asp Phe Gly Met Tyr Phe Cys Gln Gln Ser Gly Trp Pro His
             85                  90                  95

ACG TTC GGA GGG GGG ACC AAG CTG GAA ATT AAG                           321
Thr Phe Gly Gly Gly Thr Lys Leu Glu Ile Lys
                100                 105
```

```
GAG ATT GTG CTA ACT CAG TCT CCA GCC ACC CTG TCT CTC AGC CCA GGA    48
Glu Ile Val Leu Thr Gln Ser Pro Ala Thr Leu Ser Leu Ser Pro Gly
 1           5                   10                  15

GAA AGG GCG ACT CTT TCC TGC CAG GCC AGT CAA AGT ATT AGC AAC CAC    96
Glu Arg Ala Thr Leu Ser Cys Gln Ala Ser Gln Ser Ile Ser Asn His
         20                  25                  30

CTA CAC TGG TAT CAA CAA AAA CAA CCA GGT CGG GCC CCT AGG CTT CTC   144
Leu His Trp Tyr Gln Gln Lys Gln Pro Gly Arg Ala Pro Arg Leu Leu
             35                  40                  45

CGT/ATG TAT CGT TCC CAG TCC ATC TCT GGG ATC CCC GCC AGG TTC AGT    192
Arg/Met Tyr Arg Ser Gln Ser Ile Ser Gly Ile Pro Ala Arg Phe Ser
50                       55                  60

AGT GGA TCA GGG ACA GAT TTC ACT CTC ACC ATC AGC AGT CTG GAG CCT   240
Ser Gly Ser Gly Thr Asp Phe Thr Leu Thr Ile Ser Ser Leu Glu Pro
 65                  70                  75                  80

GAA GAT TTT GCA GTC TAT TAC TGT CAA CAG TAC AGT GGC AGC TGG CCT   288
Glu Asp Phe Ala Val Tyr Tyr Cys Gln Gln Tyr Ser Gly Ser Trp Pro
             85                  90                  95

ACG TTC GGA GGG GGG ACC AAG GTG GAA ATT AAG                        321
Thr Phe Gly Gly Gly Thr Lys Val Glu Ile Lys
             100                 105
```

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
          (A) LENGTH: 351 base pairs
          (B) TYPE: nucleic acid
          (C) STRANDEDNESS: single
          (D) TOPOLOGY: linear (ix) FEATURE:
          (A) NAME/KEY: CDS
          (B) LOCATION: 1..351

(xi) SEQUENCE DESCRIPTION: SEQ ID NO: 1:

```
CAG GTG CAG CTG GTG GAG TCT GGG GGA GGC GTT GTG CAG CCT GGA AGG      48
Gln Val Gln Leu Val Glu Ser Gly Gly Gly Val Val Gln Pro Gly Arg
 1               5                  10                  15

TCC CTG AGA CTC TCC TGT GCA GCC TCT GGA TTC ACC TTC AGT AGC TAT      96
Ser Leu Arg Leu Ser Cys Ala Ala Ser Gly Phe Thr Phe Ser Ser Tyr
                20                  25                  30

GAC ATG TCT TGG GTT CGC CAG GCT CCG GGC AAG GGT CTG GAG TGG GTC     144
Asp Met Ser Trp Val Arg Gln Ala Pro Gly Lys Gly Leu Glu Trp Val
            35                  40                  45

GCA AAA GTT AGT AGT GGT GGT GGT AGC ACC TAC TAT TTA GAC ACT GTG     192
Ala Lys Val Ser Ser Gly Gly Gly Ser Thr Tyr Tyr Leu Asp Thr Val
        50                  55                  60

CAG GGC CGA TTC ACC ATC TCC AGA GAC AAT AGT AAG AAC ACC CTA TAC     240
Gln Gly Arg Phe Thr Ile Ser Arg Asp Asn Ser Lys Asn Thr Leu Tyr
65                  70                  75                  80

CTG CAA ATG AAC TCT CTG AGA GCC GAG GAC ACA GCC GTG TAT TAC TGT     288
Leu Gln Met Asn Ser Leu Arg Ala Glu Asp Thr Ala Val Tyr Tyr Cys
                85                  90                  95

GCA AGA CAT AAC TAC GGC AGT TTT GCT TAC TGG GGC CAA GGG ACT ACA     336
Ala Arg His Asn Tyr Gly Ser Phe Ala Tyr Trp Gly Gln Gly Thr Thr
               100                 105                 110

GTG ACT GTT TCT AGT                                                  351
Val Thr Val Ser Ser
            115
```

(2) INFORMATION FOR SEQ ID NO: 2:

(i) SEQUENCE CHARACTERISTICS:
          (A) LENGTH: 117 amino acids
          (B) TYPE: amino acid
          (D) TOPOLOGY: linear (ii) MOLECULE TYPE: protein (xi) SEQUENCE DESCRIPTION: SEQ ID NO: 2:

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Lys Val Ser Ser Gly Gly Gly Ser Thr Tyr Tyr Leu Asp Thr Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Asn Tyr Gly Ser Phe Ala Tyr Trp Gly Gln Gly Thr Thr
            100                 105                 110

Val Thr Val Ser Ser
        115
```

(2) INFORMATION FOR SEQ ID NO: 3:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..321

(xi) SEQUENCE DESCRIPTION: SEQ ID NO: 3:

```
GAG ATT GTG CTA ACT CAG TCT CCA GCC ACC CTG TCT CTC AGC CCA GGA      48
Glu Ile Val Leu Thr Gln Ser Pro Ala Thr Leu Ser Leu Ser Pro Gly
 1               5                  10                  15

GAA AGG GCG ACT CTT TCC TGC CAG GCC AGC CAA AGT ATT AGC AAC CAC      96
Glu Arg Ala Thr Leu Ser Cys Gln Ala Ser Gln Ser Ile Ser Asn His
            20                  25                  30

CTA CAC TGG TAT CAA CAA AGG CCT GGT CAA GCC CCA AGG CTT CTC ATC     144
Leu His Trp Tyr Gln Gln Arg Pro Gly Gln Ala Pro Arg Leu Leu Ile
        35                  40                  45

AAG TAT CGT TCC CAG TCC ATC TCT GGG ATC CCC GCC AGG TTC AGT GGC     192
Lys Tyr Arg Ser Gln Ser Ile Ser Gly Ile Pro Ala Arg Phe Ser Gly
    50                  55                  60

AGT GGA TCA GGG ACA GAT TTC ACC CTC ACT ATC TCC AGT CTG GAG CCT     240
Ser Gly Ser Gly Thr Asp Phe Thr Leu Thr Ile Ser Ser Leu Glu Pro
65                  70                  75                  80

GAA GAT TTT GCA GTC TAT TAC TGT CAA CAG AGT GGC AGC TGG CCT CAC     288
Glu Asp Phe Ala Val Tyr Tyr Cys Gln Gln Ser Gly Ser Trp Pro His
                85                  90                  95

ACG TTC GGA GGG GGG ACC AAG GTG GAA ATT AAG                         321
Thr Phe Gly Gly Gly Thr Lys Val Glu Ile Lys
            100                 105
```

(2) INFORMATION FOR SEQ ID NO: 4:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO: 4:

```
Glu Ile Val Leu Thr Gln Ser Pro Ala Thr Leu Ser Leu Ser Pro Gly
 1               5                  10                  15

Glu Arg Ala Thr Leu Ser Cys Gln Ala Ser Gln Ser Ile Ser Asn His
             20                  25                  30

Leu His Trp Tyr Gln Gln Arg Pro Gly Gln Ala Pro Arg Leu Leu Ile
         35                  40                  45

Lys Tyr Arg Ser Gln Ser Ile Ser Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Gly Ser Trp Pro His
                 85                  90                  95

Thr Phe Gly Gly Gly Thr Lys Val Glu Ile Lys
                100                 105
```

(2) INFORMATION FOR SEQ ID NO: 5:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..351

(xi) SEQUENCE DESCRIPTION: SEQ ID NO: 5:

```
GAA GTG CAG CTG GTG GAG TCT GGG GGA GGC TTA GTG AAG CCT GGA AGG      48
Glu Val Gln Leu Val Glu Ser Gly Gly Gly Leu Val Lys Pro Gly Arg
 1               5                  10                  15

TCC CTG AGA CTC TCC TGT GCA GCC TCT GGA TTC GCT TTC AGT AGC TAT      96
Ser Leu Arg Leu Ser Cys Ala Ala Ser Gly Phe Ala Phe Ser Ser Tyr
             20                  25                  30

GAC ATG TCT TGG GTT CGC CAG ATT CCG GAG AAG AGG CTG GAG TGG GTC     144
Asp Met Ser Trp Val Arg Gln Ile Pro Glu Lys Arg Leu Glu Trp Val
         35                  40                  45

GCA AAA GTT AGT AGT GGT GGT GGT AGC ACC TAC TAT TTA GAC ACT GTG     192
Ala Lys Val Ser Ser Gly Gly Gly Ser Thr Tyr Tyr Leu Asp Thr Val
     50                  55                  60

CAG GGC CGA TTC ACC ATC TCC AGA GAC AAT GCC AAG AAC ACC CTA TAC     240
Gln Gly Arg Phe Thr Ile Ser Arg Asp Asn Ala Lys Asn Thr Leu Tyr
 65                  70                  75                  80

CTG CAA ATG AGC AGT CTG AAC TCT GAG GAC ACA GCC ATG TAT TAC TGT     288
Leu Gln Met Ser Ser Leu Asn Ser Glu Asp Thr Ala Met Tyr Tyr Cys
                 85                  90                  95

GCA AGA CAT AAC TAC GGC AGT TTT GCT TAC TGG GGC CAA GGG ACT CTG     336
Ala Arg His Asn Tyr Gly Ser Phe Ala Tyr Trp Gly Gln Gly Thr Leu
                100                 105                 110

GTC ACT GTC TCT GCA                                                  351
Val Thr Val Ser Ala
        115
```

(2) INFORMATION FOR SEQ ID NO: 6:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 6:

```
Glu Val Gln Leu Val Glu Ser Gly Gly Gly Leu Val Lys Pro Gly Arg
 1               5                  10                  15

Ser Leu Arg Leu Ser Cys Ala Ala Ser Gly Phe Ala Phe Ser Ser Tyr
            20                  25                  30

Asp Met Ser Trp Val Arg Gln Ile Pro Glu Lys Arg Leu Glu Trp Val
         35                  40                  45

Ala Lys Val Ser Ser Gly Gly Gly Ser Thr Tyr Tyr Leu Asp Thr Val
     50                  55                  60

Gln Gly Arg Phe Thr Ile Ser Arg Asp Asn Ala Lys Asn Thr Leu Tyr
 65                  70                  75                  80

Leu Gln Met Ser Ser Leu Asn Ser Glu Asp Thr Ala Met Tyr Tyr Cys
                85                  90                  95

Ala Arg His Asn Tyr Gly Ser Phe Ala Tyr Trp Gly Gln Gly Thr Leu
            100                 105                 110

Val Thr Val Ser Ala
        115
```

(2) INFORMATION FOR SEQ ID NO: 7:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..321

(xi) SEQUENCE DESCRIPTION: SEQ ID NO: 7:

```
GAT ATT GTG CTA ACT CAG TCT CCA GCC ACC CTG TCT GTG ACA CCA GGA    48
Asp Ile Val Leu Thr Gln Ser Pro Ala Thr Leu Ser Val Thr Pro Gly
 1               5                  10                  15

GAT AGC GTC AGT CTT TCC TGC CAG GCC AGC CAA AGT ATT AGC AAC CAC    96
Asp Ser Val Ser Leu Ser Cys Gln Ala Ser Gln Ser Ile Ser Asn His
            20                  25                  30

CTA CAC TGG TAT CAA CAA AAA TCA CAT GAG TCT CCA AGG CTT CTC ATC   144
Leu His Trp Tyr Gln Gln Lys Ser His Glu Ser Pro Arg Leu Leu Ile
         35                  40                  45

AAG TAT CGT TCC CAG TCC ATC TCT GGG ATC CCC TCC AGG TTC AGT GGC   192
Lys Tyr Arg Ser Gln Ser Ile Ser Gly Ile Pro Ser Arg Phe Ser Gly
     50                  55                  60

AGT GGA TCA GGG ACA GAT TTC GCT CTC AGT ATC AAC AGT GTG GAG ACT   240
Ser Gly Ser Gly Thr Asp Phe Ala Leu Ser Ile Asn Ser Val Glu Thr
 65                  70                  75                  80

GAA GAT TTT GGA ATG TAT TTC TGT CAA CAG AGT GGC AGC TGG CCT CAC   288
Glu Asp Phe Gly Met Tyr Phe Cys Gln Gln Ser Gly Ser Trp Pro His
                85                  90                  95

ACG TTC GGA GGG GGG ACC AAG CTG GAA ATT AAG                       321
Thr Phe Gly Gly Gly Thr Lys Leu Glu Ile Lys
            100                 105
```

(2) INFORMATION FOR SEQ ID NO: 8:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO: 8:

Asp Ile Val Leu Thr Gln Ser Pro Ala Thr Leu Ser Val Thr Pro Gly
1               5                   10                  15

Asp Ser Val Ser Leu Ser Cys Gln Ala Ser Gln Ser Ile Ser Asn His
            20                  25                  30

Leu His Trp Tyr Gln Gln Lys Ser His Glu Ser Pro Arg Leu Leu Ile
        35                  40                  45

Lys Tyr Arg Ser Gln Ser Ile Ser Gly Ile Pro Ser Arg Phe Ser Gly
    50                  55                  60

Ser Gly Ser Gly Thr Asp Phe Ala Leu Ser Ile Asn Ser Val Glu Thr
65              70                  75                  80

Glu Asp Phe Gly Met Tyr Phe Cys Gln Gln Ser Gly Ser Trp Pro His
            85                  90                  95

Thr Phe Gly Gly Gly Thr Lys Leu Glu Ile Lys
        100                 105

(2) INFORMATION FOR SEQ ID NO: 9:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO: 9:

CAGGTGCAGC TGGTGGAGTC TGGGGGAGGC GTTGTGCAGC CTGGAAGGTC CCTGAGACTC        60

TCCTGTGCAG CCTCTGGATT CACC                                              84

(2) INFORMATION FOR SEQ ID NO: 10:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO: 10:

AACTTTTGCG ACCCACTCCA GACCCTTGCC CGGAGCCTGG CGAACCCAAG ACATGTCATA        60

GCTACTGAAG GTGAATCCAG AGGC                                              84

(2) INFORMATION FOR SEQ ID NO: 11:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO: 11:

TGGGTCGCAA AAGTTAGTAG TGGTGGTGGT AGCACCTACT ATTTAGACAC TGTGCAGGGC        60

CGATTCACCA TCTCCAGAGA CAATAGT                                           87

(2) INFORMATION FOR SEQ ID NO: 12:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 12:

TGCACAGTAA TACACGGCTG TGTCCTCGGC TCTCAGAGAG TTCATTTGCA GGTATAGGGT        60

GTTCTTACTA TTGTCTCTGG A        81

(2) INFORMATION FOR SEQ ID NO: 13:

(i) SEQUENCE CHARACTERISTICS:
            (A) LENGTH: 75 base pairs
            (B) TYPE: nucleic acid
            (C) STRANDEDNESS: single
            (D) TOPOLOGY: linear (xi) SEQUENCE DESCRIPTION: SEQ ID NO: 13:

GTGTATTACT GTGCAAGACA TAACTACGGC AGTTTTGCTT ACTGGGGCCA AGGGACTACA        60

GTGACTGTTT CTAGT        75

(2) INFORMATION FOR SEQ ID NO: 14:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (xi) SEQUENCE DESCRIPTION: SEQ ID NO: 14:

GAGATTGTGC TAACTCAGTC TCCAGCCACC CTGTCTCTCA GCCCAGGAGA AAGGGCGACT        60

CTTTCCTGCC AGGCCAGCCA AAGTATT        87

(2) INFORMATION FOR SEQ ID NO: 15:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (xi) SEQUENCE DESCRIPTION: SEQ ID NO: 15:

GATGAGAAGC CTTGGGGCTT GACCAGGCCT TTGTTGATAC CAGTGTAGGT GGTTGCTAAT        60

ACTTTGGCTG GC        72

(2) INFORMATION FOR SEQ ID NO: 16:

(i) SEQUENCE CHARACTERISTICS:
            (A) LENGTH: 84 base pairs
            (B) TYPE: nucleic acid
            (C) STRANDEDNESS: single
            (D) TOPOLOGY: linear (xi) SEQUENCE DESCRIPTION: SEQ ID NO: 16:

CCAAGGCTTC TCATCWASTA TCGTTCCCAG TCCATCTCTG GGATCCCCGC CAGGTTCAGT        60

GGCAGTGGAT CAGGGACAGA TTTC        84

(2) INFORMATION FOR SEQ ID NO: 17:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (xi) SEQUENCE DESCRIPTION: SEQ ID NO: 17:

GCTGCCACTC TGTTGACAGW AATAGACTGC AAAATCTTCA GGCTCCAGAC TGGAGATAGT  60

GAGGGTGAAA TCTGTCCCTG A  81

(2) INFORMATION FOR SEQ ID NO: 18:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO: 18:

CAACAGAGTG GCAGCTGGCC TCACACGTTC GGAGGGGGGA CCAAGGTGGA AATTAAG  57

(2) INFORMATION FOR SEQ ID NO: 19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 19:

GCCCAACCAG CCATGGCCGA TATTGTGCTA ACTCAG  36

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 20:

ACAGTTGGTG CAGCATCAGC  20

(2) INFORMATION FOR SEQ ID NO: 21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 21:

ACCCCTGTGG CAAAAGCCGA AGTGCAGCTG GTGGAG  36

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 22:

GATGGGGGTG TCGTTTTGGC  20

(2) INFORMATION FOR SEQ ID NO: 23:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO: 23:

GAGATTGTGC TAACTCAGTC TCCAGCCACC CTGTCTCTCA GCCCAGGAGA AAGGGCGACT    60

CTTTCCTGCC AGGCCAGCCA AAGTATT    87

(2) INFORMATION FOR SEQ ID NO: 24:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO: 24:

TTAGATGAGA AGCCTTGGGG CTTGACCAGG CCTTTGTTGA TACCAGTGTA GGTGGTTGCT    60

AATACTTTGG CTGGC    75

(2) INFORMATION FOR SEQ ID NO: 25:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO: 25:

CCAAGGCTTC TCATCTAATA TCGTTCCCAG TCCATCTCTG GGATCCCCGC CAGGTTCAGT    60

GGCAGTGGAT CAGGGACAGA TTTC    84

(2) INFORMATION FOR SEQ ID NO: 26:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 26:

GCTGCCACTC TGTTGACAGT AATAGACTGC AAAATCTTCA GGCTCCAGAC TGGAGATAGT    60

GAGGGTGAAA TCTGTCCCTG A    81

(2) INFORMATION FOR SEQ ID NO: 27:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO: 27:

CAACAGAGTG GCAGCTGGCC TCACACGTTC GGAGGGGGGA CCAAGGTGGA AATTAAG    57

(2) INFORMATION FOR SEQ ID NO: 28:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 28:

Tyr Pro Tyr Asp Val Pro Asp Tyr Ala Ser
1               5                   10

(2) INFORMATION FOR SEQ ID NO: 29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 29:

```
GCTACTGAAG GCGAATCCAG AG                                         22
```

(2) INFORMATION FOR SEQ ID NO: 30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 11..13
        (D) OTHER INFORMATION: /note= ""NNN" represents a codon
            specifying any amino acid other than Lys."

(xi) SEQUENCE DESCRIPTION: SEQ ID NO: 30:

```
GGGAACGATA NNNGATGAGA AGC                                        23
```

(2) INFORMATION FOR SEQ ID NO: 31:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..321

(xi) SEQUENCE DESCRIPTION: SEQ ID NO: 31:

```
GAG ATT GTG CTA ACT CAG TCT CCA GCC ACC CTG TCT CTC AGC CCA GGA      48
Glu Ile Val Leu Thr Gln Ser Pro Ala Thr Leu Ser Leu Ser Pro Gly
 1               5                  10                  15

GAA AGG GCG ACT CTT TCC TGC CAG GCC AGC CAA AGT ATT AGC AAC CAC      96
Glu Arg Ala Thr Leu Ser Cys Gln Ala Ser Gln Ser Ile Ser Asn His
             20                  25                  30

CTA CAC TGG TAT CAA CAA AGG CCT GGT CAA GCC CCA AGG CTT CTC ATC     144
Leu His Trp Tyr Gln Gln Arg Pro Gly Gln Ala Pro Arg Leu Leu Ile
         35                  40                  45

MKK TAT CGT TCC CAG TCC ATC TCT GGG ATC CCC GCC AGG TTC AGT GGC     192
Xaa Tyr Arg Ser Gln Ser Ile Ser Gly Ile Pro Ala Arg Phe Ser Gly
     50                  55                  60

AGT GGA TCA GGG ACA GAT TTC ACC CTC ACT ATC TCC AGT CTG GAG CCT     240
Ser Gly Ser Gly Thr Asp Phe Thr Leu Thr Ile Ser Ser Leu Glu Pro
 65                  70                  75                  80

GAA GAT TTT GCA GTC TAT TAC TGT CAA CAG AGT GGC AGC TGG CCT CAC     288
Glu Asp Phe Ala Val Tyr Tyr Cys Gln Gln Ser Gly Ser Trp Pro His
                 85                  90                  95

ACG TTC GGA GGG GGG ACC AAG GTG GAA ATT AAG                         321
Thr Phe Gly Gly Gly Thr Lys Val Glu Ile Lys
                100                 105
```

-continued (2) INFORMATION FOR SEQ ID NO: 32:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO: 32:

```
Glu Ile Val Leu Thr Gln Ser Pro Ala Thr Leu Ser Leu Ser Pro Gly
 1               5                  10                  15

Glu Arg Ala Thr Leu Ser Cys Gln Ala Ser Gln Ser Ile Ser Asn His
             20                  25                  30

Leu His Trp Tyr Gln Gln Arg Pro Gly Gln Ala Pro Arg Leu Leu Ile
         35                  40                  45

Xaa Tyr Arg Ser Gln Ser Ile Ser Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Gly Ser Trp Pro His
                 85                  90                  95

Thr Phe Gly Gly Gly Thr Lys Val Glu Ile Lys
                100                 105
```

US 7,422,744 B2

METHODS OF TREATING CANCER WITH ALPHAVBETA3-SPECIFIC ANTIBODIES

This application is a continuation of application Ser. No. 08/791,391, now issued as U.S. Pat. No. 6,590,079, filed Jan. 30, 1997, which is incorporated by reference in its entirety.

BACKGROUND OF THE INVENTION

The present invention relates generally to integrin mediated diseases and, more particularly, to nucleic acids encoding $\alpha_v\beta_3$-inhibitory monoclonal antibodies and to CDR grafted $\alpha_v\beta_3$-inhibitory antibodies for the therapeutic treatment of $\alpha_v\beta_3$-mediated diseases.

Integrins are a class of cell adhesion receptors that mediate both cell-cell and cell-extracellular matrix adhesion events. Integrins consist of heterodimeric polypeptides where a single $\alpha$ chain polypeptide noncovalently associates with a single $\beta$ chain. There are now about 14 distinct $\alpha$ chain polypeptides and at least about 8 different $\beta$ chain polypeptides which constitute the integrin family of cell adhesion receptors. In general, different binding specificities and tissue distributions are derived from unique combinations of the $\alpha$ and $\beta$ chain polypeptides or integrin subunits. The family to which a particular integrin is associated with is usually characterized by the $\beta$ subunit. However, the ligand binding activity of the integrin is largely influenced by the $\alpha$ subunit. For example, vitronectin binding integrins contain the $\alpha_v$ integrin subunit.

It is now known that the vitronectin binding integrins consist of at least three different $\alpha_v$ containing integrins. These $\alpha_v$ containing integrins include $\alpha_v\beta_3$, $\alpha_v\beta_1$ and $\alpha_v\beta_5$, all of which exhibit different ligand binding specificities. For example, in addition to vitronectin, $\alpha_v\beta_3$ binds to a large variety of extracellular matrix proteins including fibronectin, fibrinogen, laminin, thrombospondin, von Willebrand factor, collagen, osteopontin and bone sialoprotein I. The integrin $\alpha_v\beta_1$ binds to fibronectin, osteopontin and vitronectin whereas $\alpha_v\beta_5$ is known to bind to vitronectin and osteopontin.

As cell adhesion receptors, integrins are involved in a variety of physiological processes including, for example, cell attachment, cell migration and cell proliferation. Different integrins play different roles in each of these biological processes and the inappropriate regulation of their function or activity can lead to various pathological conditions. For example, inappropriate endothelial cell proliferation during neovascularization of a tumor has been found to be mediated by cells expressing vitronectin binding integrins. In this regard, the inhibition of the vitronectin-binding integrin $\alpha_v\beta_3$ also inhibits this process of tumor neovascularization. By this same criteria, $\alpha_v\beta_3$ has also been shown to mediate the abnormal cell proliferation associated with restenosis and granulation tissue development in cutaneous wounds, for example. Additional diseases or pathological states mediated or influenced by $\alpha_v\beta_3$ include, for example, metastasis, osteoporosis, age-related macular degeneration and diabetic retinopathy, and inflammatory diseases such as rheumatoid arthritis and psoriasis. Thus, agents which can specifically inhibit vitronectin-binding integrins would be valuable for the therapeutic treatment of diseases.

Many integrins mediate their cell adhesive functions by recognizing the tripeptide sequence Arg-Gly-Asp (RGD) found within a large number of extracellular matrix proteins. A variety of approaches have attempted to model agents after this sequence to target a particular integrin-mediated pathology. Such approaches include, for example, the use of RGD-containing peptides and peptide analogues which rely on specificity to be conferred by the sequences flanking the RGD core tripeptide sequence. Although there has been some limited success, most RGD-based inhibitors have been shown to be, at most, selective for the targeted integrin and therefore exhibit some cross-reactivity to other non-targeted integrins. Such cross-reactive inhibitors therefore lack the specificity required for use as an efficacious therapeutic. This is particularly true for previously identified inhibitors of the integrin $\alpha_v\beta_3$.

Monoclonal antibodies on the other hand exhibit the specificity required to be used as an effective therapeutic. Antibodies also have the advantage in that they can be routinely generated against essentially any desired antigen. Moreover, with the development of combinatorial libraries, antibodies can now be produced faster and more efficiently than by previously used methods within the art. The use of combinatorial methodology also allows for the selection of the desired antibody along with the simultaneous isolation of the encoding heavy and light chain nucleic acids. Thus, further modification can be performed to the combinatorial antibody without the incorporation of an additional cloning step.

Regardless of the potential advantages associated with the use of monoclonal antibodies as therapeutics, these molecules nevertheless have the drawback in that they are almost exclusively derived from non-human mammalian organisms. Therefore, their use as therapeutics is limited by the fact that they will normally elicit a host immune response. Methods for substituting the antigen binding site or complementarity determining regions (CDRs) of the non-human antibody into a human framework have been described. Such methods vary in terms of which amino acid residues should be substituted as the CDR as well as which framework residues should be changed to maintain binding specificity. In this regard, it is understood that proper orientation of the $\beta$ sheet architecture, correct packing of the heavy and light chain interface and appropriate conformation of the CDRs are all important for preserving antigen specificity and affinity within the grafted antibody. However, all of these methods require knowledge of the nucleotide and amino acid sequence of the non-human antibody and the availability of an appropriately modeled human framework.

Thus, there exists a need for the availability of nucleic acids encoding integrin inhibitory antibodies which can be used as compatible therapeutics in humans. For $\alpha_v\beta_3$-mediated diseases, the present invention satisfies this need and provides related advantages as well.

SUMMARY OF THE INVENTION

The invention provides a Vitaxin antibody and a LM609 grafted antibody exhibiting selective binding affinity to $\alpha_v\beta_3$. The Vitaxin antibody consists of at least one Vitaxin heavy chain polypeptide and at least one Vitaxin light chain polypeptide or functional fragments thereof. Also provided are the Vitaxin heavy and light chain polypeptides and functional fragments. The LM609 grafted antibody consists of at least one LM609 CDR grafted heavy chain polypeptide and at least one LM609 CDR grafted light chain polypeptide or functional fragment thereof. Nucleic acids encoding Vitaxin and LM609 grafted heavy and light chains as well as nucleic acids encoding the parental non-human antibody LM609 are additionally provided. Functional fragments of such encoding nucleic acids are similarly provided. The invention also provides a method of inhibiting a function of $\alpha_v\beta_3$. The method consists of contacting $\alpha_v\beta_3$ with Vitaxin or a LM609 grafted antibody or functional fragments thereof under conditions which allow binding to $\alpha_v\beta_3$. Finally, the invention provides for a method of treating an $\alpha_v\beta_3$-mediated disease. The method consists of administering an effective amount of Vitaxin or a LM609 grafted antibody or functional fragment thereof under conditions which allow binding to $\alpha_v\beta_3$.

BRIEF DESCRIPTION OF THE DRAWINGS

FIG. 1 shows the nucleotide and deduced amino acid sequence of the variable region of the antibody Vitaxin. FIG. 1A shows the nucleotide and deduced amino acid sequences for the Vitaxin heavy chain variable region (Gln1-Ser117; SEQ ID NOS:1 and 2, respectively) while FIG. 1B shows the nucleotide and deduced amino acid sequences for the Vitaxin light chain variable region (Glu1-Lys107; SEQ ID NOS:3 and 4, respectively).

FIG. 2 shows the nucleotide and deduced amino acid sequence of the variable region of the monoclonal antibody LM609. FIG. 2A shows the nucleotide and deduced amino acid sequence of the LM609 heavy chain variable region (SEQ ID NOS:5 and 6, respectively). The variable region extends from amino acid Glu1 to Ala117. FIG. 2B shows the nucleotide and deduced amino acid sequence of the LM609 light chain variable region (SEQ ID NOS:7 and 8, respectively). The variable region of the light chain extends from amino acid Asp1 to Lys107.

FIG. 4 shows the characterization of Vitaxin binding specificity.

FIG. 6 shows the reduction in tumor growth due to Vitaxin mediated inhibition of neovascularization.

FIG. 7 shows the nucleotide and deduced amino acid sequence of the light chain variable region of the LM609 grafted antibody fragment (Glu1-Lys107; SEQ ID NOS:31 and 32, respectively). Position 49 of the light chain variable region can at least be either Arg or Met. The nucleotide and deduced amino acid sequence of the heavy chain variable region of the LM609 grafted antibody fragment is shown in FIG. 1A (SEQ ID NOS:1 and 2, respectively).

DETAILED DESCRIPTION OF THE INVENTION

Figure 3:
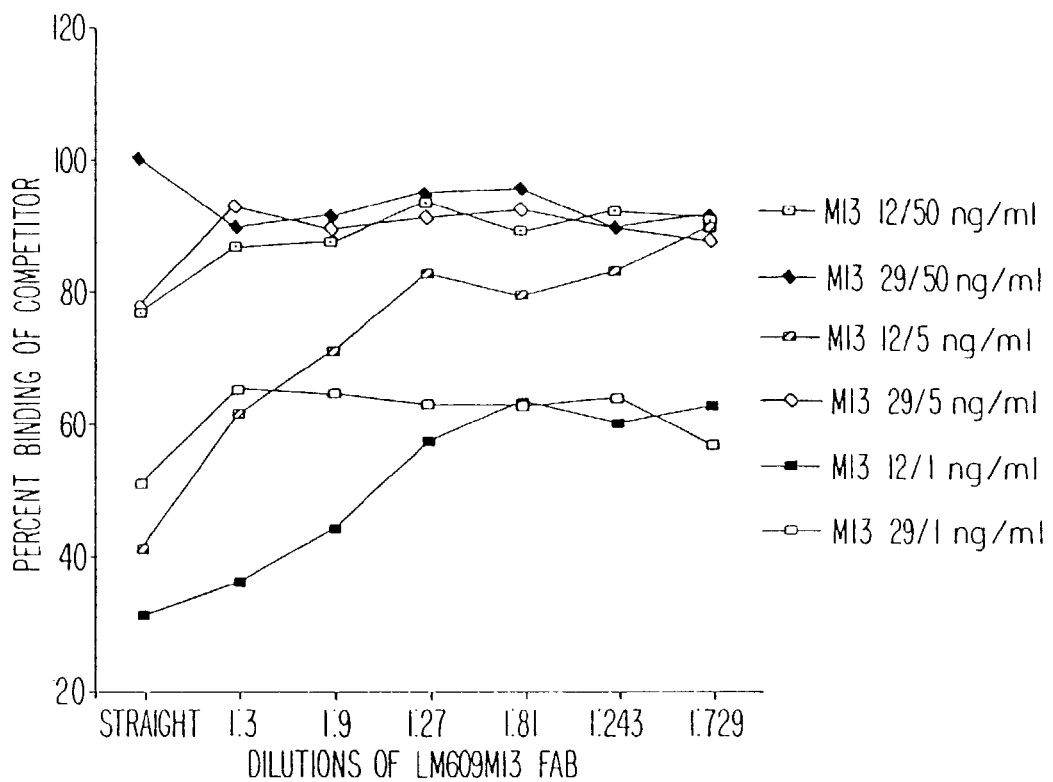
FIG. 3 shows the competitive inhibition of LM609 IgG binding to the integrin $\alpha_v\beta_3$ with recombinant LM609 Fab. Soluble recombinant murine LM609 Fab fragments were prepared from periplasmic fractions of M13 bacteriophage clones muLM609M13 12 and muLM609M13 29. The periplasm samples were serially diluted, mixed with either 1 ng/ml, 5 ng/ml, or 50 ng/ml of LM609 IgG and then incubated in 96 well plates coated with purified $\alpha_v\beta_3$. Plates were washed and bound LM609 IgG detected with goat anti-murine Fc specific antibody conjugated to alkaline phosphatase. Fab produced by clone muLM609M13 12 inhibits both 1 ng/ml and 5 ng/ml LM609 IgG binding at all concentrations of Fab greater than 1:27 dilution.

The invention is directed to nucleic acids encoding the monoclonal antibody (MAb) LM609. This antibody specifically recognizes the integrin $\alpha_v\beta_3$ and inhibits its functional activity. The invention is also directed to nucleic acids encoding and to polypeptides comprising non-murine grafted forms of LM609. These grafted antibodies retain the binding specificity and inhibitory activity of the parent murine antibody LM609.

In one embodiment, the hybridoma expressing LM609 was used as a source to generate and clone cDNAs encoding LM609. The heavy and light chain encoding cDNAs were sequenced and their CDR regions were substituted into a human antibody framework to generate the non-murine form of the antibody. The substitution or grafting of the CDRs was performed by codon-based mutagenesis to generate a combinatorial antibody Fab library consisting of members that presented alternative residues at certain positions. Screening of the library resulted in the isolation of Vitaxin. As a grafted antibody containing human framework sequences, it is unlikely that Vitaxin will elicit a host immune response and can therefore be advantageously used for the treatment of $\alpha_v\beta_3$-mediated diseases.

As used herein, the term "monoclonal antibody LM609" or "LM609" is intended to mean the murine monoclonal antibody specific for the integrin $\alpha_v\beta_3$ which is described by Cheresh, D.A. *Proc. Natl. Acad. Sci. USA* 84:6471-6475 (1987) and by Cheresh and Spiro *J. Biol. Chem.* 262:17703-17711 (1987). LM609 was produced against and is reactive with the M21 cell adhesion receptor now known as the integrin $\alpha_v\beta_3$. LM609 inhibits the attachment of M21 cells to $\alpha_v\beta_3$ ligands such as vitronectin, fibrinogen and von Willebrand factor (Cheresh and Spiro, supra) and is also an inhibitor of $\alpha_v\beta_3$-mediated pathologies such as tumor induced angiogenesis (Brooks et al. *Cell* 79:1157-1164 (1994), granulation tissue development in cutaneous wound (Clark et al., *Am. J. Pathology,* 148:1407-1421 (1996)) and smooth muscle cell migration such as that occurring during restenosis (Choi et al., *J. Vascular Surg.,* 19:125-134 (1994); Jones et al., *Proc. Natl. Acad. Sci.* 93:2482-2487 (1996)).

As used herein, the term "Vitaxin" is intended to refer to a non-mouse antibody or functional fragment thereof having substantially the same heavy and light chain CDR amino acid sequences as found in LM609. The term "Vitaxin" when used in reference to heavy or light chain polypeptides is intended to refer to a non-mouse heavy or light chain or functional fragment thereof having substantially the same heavy or light chain CDR amino acid sequences as found in the heavy or light chain of LM609, respectively. When used in reference to a functional fragment, not all LM609 CDRs need to be represented. Rather, only those CDRs that would normally be present in the antibody portion that corresponds to the functional fragment are intended to be referenced as the LM609 CDR amino acid sequences in the Vitaxin functional fragment. Similarly, the use of the term "Vitaxin" in reference to an encoding nucleic acid is intended to refer to a nucleic acid encoding a non-mouse antibody or functional fragment having substantially the same nucleotide sequence as the heavy and light chain CDR nucleotide sequences and encoding substantially the same CDR amino acid sequences as found in LM609.

As used herein, the term "LM609 grafted antibody" is intended to refer to a non-mouse antibody or functional fragment thereof having substantially the same heavy and light chain CDR amino acid sequences as found in LM609 and absent of the substitution of LM609 amino acid residues outside of the CDRs as defined by Kabat et al., U.S. Dept. of Health and Human Services, "Sequences of Proteins of Immunological Interest" (1983). The term "LM609 grafted antibody" or "LM609 grafted" when used in reference to heavy or light chain polypeptides is intended to refer to a non-mouse heavy or light chain or functional fragment thereof having substantially the same heavy or light chain CDR amino acid sequences as found in the heavy or light chain of LM609, respectively, and also absent of the substitution of LM609 residues outside of the CDRs as defined by Kabat et al., supra. When used in reference to a functional fragment, not all LM609 CDRs need to be represented. Rather, only those CDRs that would normally be present in the antibody portion that corresponds to the functional fragment are intended to be referenced as the LM609 CDR amino acid sequences in the LM609 grafted functional fragment. Similarly, the term "LM609 grafted antibody" or "LM609 grafted" used in reference to an encoding nucleic acid is intended to refer to a nucleic acid encoding a non-mouse antibody or functional fragment being absent of the substitution of LM609 amino acids outside of the CDRs as defined by Kabat et al., supra and having substantially the same nucleotide sequence as the heavy and light chain CDR nucleotide sequences and encoding substantially the same CDR amino acid sequences as found in LM609 and as defined by Kabat et al., supra.

The term "grafted antibody" or "grafted" when used in reference to heavy or light chain polypeptides or functional fragments thereof is intended to refer to a heavy or light chain or functional fragment thereof having substantially the same heavy or light chain of a donor antibody, respectively, and also absent of the substitution of donor amino acid residues outside of the CDRs as defined by Kabat et al., supra. When used in reference to a functional fragment, not all donor CDRs need to be represented. Rather, only those CDRs that would normally be present in the antibody portion that corresponds to the functional fragment are intended to be referenced as the donor CDR amino acid sequences in the functional fragment. Similarly, the term "grafted antibody" or "grafted" when used in reference to an encoding nucleic acid is intended to refer to a nucleic acid encoding an antibody or functional fragment, being absent of the substitution of donor amino acids outside of the CDRs as defined by Kabat et al., supra and having substantially the same nucleotide sequence as the heavy and light chain CDR nucleotide sequences and encoding substantially the same CDR amino acid sequences as found in the donor antibody and as defined by Kabat et al., supra.

The meaning of the above terms are intended to include minor variations and modifications of the antibody so long as its function remains uncompromised. Functional fragments such as Fab, F(ab)$_2$, Fv, single chain Fv (scFv) and the like are similarly included within the definition of the terms LM609 and Vitaxin. Such functional fragments are well known to those skilled in the art. Accordingly, the use of these terms in describing functional fragments of LM609 or the Vitaxin antibody are intended to correspond to the definitions well known to those skilled in the art. Such terms are described in, for example, Harlow and Lane, *Antibodies: A Laboratory Manual*, Cold Spring Harbor Laboratory, New York (1989); *Molec. Biology and Biotechnology: A Comprehensive Desk Reference* (Myers, R. A. (ed.), New York: VCH Publisher, Inc.); Huston et al., *Cell Biophysics*, 22:189-224 (1993); Plückthun and Skerra, *Meth. Enzymol.*, 178:497-515 (1989) and in Day, E. D., *Advanced Immunochemistry*, Second Ed., Wiley-Liss, Inc., New York, N.Y. (1990).

As with the above terms used for describing functional fragments of LM609, Vitaxin and a LM609 grafted antibody, the use of terms which reference other LM609, Vitaxin or LM609 grafted antibody domains, functional fragments, regions, nucleotide and amino acid sequences and polypeptides or peptides, is similarly intended to fall within the scope of the meaning of each term as it is known and used within the art. Such terms include, for example, "heavy chain polypeptide" or "heavy chain", "light chain polypeptide" or "light chain", "heavy chain variable region" ($V_H$) and "light chain variable region" ($V_L$) as well as the term "complementarity determining region" (CDR).

In the case where there are two or more definitions of a term which is used and/or accepted within the art, the definition of the term as used herein is intended to include all such meanings unless explicitly stated to the contrary. A specific example is the use of the term "CDR" to describe the non-contiguous antigen combining sites found within the variable region of both heavy and light chain polypeptides. This particular region has been described by Kabat et al., supra, and by Chothia et al., *J. Mol. Biol.* 196:901-917 (1987) and by MacCallum et al., *J. Mol. Biol.* 262:732-745 (1996) where the definitions include overlapping or subsets of amino acid residues when compared against each other. Nevertheless, application of either definition to refer to a CDR of LM609, Vitaxin, LM609 grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

| | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Clothia et al., supra
[3]Residue numbering follows the nomenclature of MacCallum et al., supra As used herein, the term "substantially" or "substantially the same" when used in reference to a nucleotide or amino acid sequence is intended to mean that the nucleotide or amino acid sequence shows a considerable degree, amount or extent of sequence identity when compared to a reference sequence. Such considerable degree, amount or extent of sequence identity is further considered to be significant and meaningful and therefore exhibit characteristics which are definitively recognizable or known. Thus, a nucleotide sequence which is substantially the same nucleotide sequence as a heavy or light chain of LM609, Vitaxin, or a LM609 grafted antibody including fragments thereof, refers to a sequence which exhibits characteristics that are definitively known or recognizable as encoding or as being the amino acid sequence of LM609, Vitaxin or a LM609 grafted antibody. Minor modifications thereof are included so long as they are recognizable as a LM609, Vitaxin or a LM609 grafted antibody sequence. Similarly, an amino acid sequence which is substantially the same amino acid sequence as a heavy or light chain of Vitaxin, a LM609 grafted antibody or functional fragment thereof, refers to a sequence which exhibits characteristics that are definitively known or recognizable as representing the amino acid sequence of Vitaxin or a LM609 grafted antibody and minor modifications thereof.

As used herein, the term "fragment" when used in reference to a nucleic acid encoding LM609, Vitaxin or a LM609 grafted antibody is intended to mean a nucleic acid having substantially the same sequence as a portion of a nucleic acid encoding LM609, Vitaxin or a LM609 grafted antibody. The nucleic acid fragment is sufficient in length and sequence to selectively hybridize to an LM609, a Vitaxin or a LM609 grafted antibody encoding nucleic acid or a nucleotide sequence that is complementary to an LM609, Vitaxin or LM609 grafted antibody encoding nucleic acid. Therefore, fragment is intended to include primers for sequencing and polymerase chain reaction (PCR) as well as probes for nucleic acid blot or solution hybridization. The meaning of the term is also intended to include regions of nucleotide sequences that do not directly encode LM609 polypeptides such as the introns, and the untranslated region sequences of the LM609 encoding gene.

As used herein, the term "functional fragment" when used in reference to Vitaxin, to a LM609 grafted antibody or to heavy or light chain polypeptides thereof is intended to refer to a portion of Vitaxin or a LM609 grafted antibody including heavy or light chain polypeptides which still retains some or all or the $\alpha_v\beta_3$ binding activity, $\alpha_v\beta_3$ binding specificity and/or integrin $\alpha_v\beta_3$-inhibitory activity. Such functional fragments can include, for example, antibody functional fragments such as Fab, F(ab)$_2$, Fv, single chain Fv (scFv) Other functional fragments can include, for example, heavy or light chain polypeptides, variable region polypeptides or CDR polypeptides or portions thereof so long as such functional fragments retain binding activity, specificity or inhibitory activity. The term is also intended to include polypeptides encompassing, for example, modified forms of naturally occurring amino acids such as D-stereoisomers, non-naturally occurring amino acids, amino acid analogues and mimetics so long as such polypeptides retain functional activity as defined above.

The invention provides a nucleic acid encoding a heavy chain polypeptide for Vitaxin or a functional fragment thereof. Also provided is a nucleic acid encoding a light chain polypeptide for Vitaxin or a functional fragment thereof. The nucleic acids consist of substantially the same heavy or light chain variable region nucleotide sequences as those shown in FIGS. 1A and 1B (SEQ ID NOS:1 and 3, respectively) or a fragment thereof.

Vitaxin, including functional fragments thereof, is a non-mouse antibody which exhibits substantially the same binding activity, binding specificity and inhibitory activity as LM609. The Vitaxin Fv Fragment was produced by functionally replacing CDRs within human heavy and light chain variable region polypeptides with the CDRs derived from LM609. Functional replacement of the CDRs was performed by recombinant methods known to those skilled in the art. Such methods are commonly referred to as CDR grafting and are the subject matter of U.S. Pat. No. 5,225,539. Such methods can also be found described in "Protein Engineering of Antibody Molecules for Prophylactic and Therapeutic Applications in Man," Clark, M. (ed.), Nottingham, England: Academic Titles (1993).

Briefly, LM609 nucleic acid fragments having substantially the same nucleotide and encoding substantially the same amino acid sequence of each of the heavy and light chain CDRs were synthesized and substituted into each of the respective human chain encoding nucleic acids. To maintain functionality of the newly derived Vitaxin antibody, modifications were performed within the non-CDR framework region. These individual changes were made by generating a population of CDR grafted heavy and light chain variable regions wherein all possible changes outside of the CDRs were represented and then selecting the appropriate antibody by screening the population for binding activity. This screen resulted in the selection of the Vitaxin antibody described herein.

The nucleotide sequences of the Vitaxin heavy and light chain variable regions are shown in FIGS. 1A and 1B, respectively. These sequences correspond substantially to those that encode the heavy and light chain variable region polypeptides of Vitaxin. These Vitaxin nucleic acids are intended to include both the sense and anti-sense strands of the Vitaxin encoding sequences. Single- and double-stranded nucleic acids are similarly included as well as non-coding portions of the nucleic acid such as introns, 5'- and 3'-untranslated regions and regulatory sequences of the gene for example.

As shown in FIG. 1A, the Vitaxin heavy chain variable region polypeptide is encoded by a nucleic acid of about 351 nucleotides in length which begins at the amino terminal Gln1 residue of the variable region through to Ser117. This Vitaxin heavy chain variable region encoding nucleic acid is joined to a human IgG$_1$ constant region to yield a coding region of 1431 nucleotides which encodes a heavy chain polypeptide of 477 total amino acids. Shown in FIG. 1B is the Vitaxin light chain variable region polypeptide which is encoded by a nucleic acid of about 321 nucleotides in length beginning at the amino terminal Glu1 residue of the variable region through to Lys107. This Vitaxin light chain variable region nucleic acid is joined to a human kappa construct region to yield a coding region of 642 nucleotides which code for a light chain polypeptide of 214 total amino acids.

Minor modification of these nucleotide sequences are intended to be included as heavy and light chain Vitaxin encoding nucleic acids and their functional fragments. Such minor modifications include, for example, those which do not change the encoded amino acid sequence due to the degeneracy of the genetic code as well as those which result in only a conservative substitution of the encoded amino acid sequence. Conservative substitutions of encoded amino acids include, for example, amino acids which belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are included within the nucleic acids encoding Vitaxin heavy and light chain polypeptides so long as the nucleic acid or encoded polypeptides retain some or all of their function as described herein.

Thus, the invention also provides a nucleic acid encoding a Vitaxin heavy chain or functional fragment thereof wherein the nucleic acid encodes substantially the same heavy chain variable region amino acid sequence of Vitaxin as that shown in FIG. 1A (SEQ ID NO:2) or a fragment thereof. Similarly, the invention also provides a nucleic acid encoding a Vitaxin light chain or functional fragment thereof wherein the nucleic acid encodes substantially the same light chain variable region amino acid sequence of Vitaxin as that shown in FIG. 1B (SEQ ID NO:4) or a fragment thereof.

In addition to conservative substitutions of amino acids, minor modifications of the Vitaxin encoding nucleotide sequences which allow for the functional replacement of amino acids are also intended to be included within the definition of the term. The substitution of functionally equivalent amino acids encoded by the Vitaxin nucleotide sequences is routine and can be accomplished by methods known to those skilled in the art. Briefly, the substitution of functionally equivalent amino acids can be made by identifying the amino acids which are desired to be changed, incorporating the changes into the encoding nucleic acid and then determining the function of the recombinantly expressed and modified Vitaxin polypeptide or polypeptides. Rapid methods for making and screening multiple simultaneous changes are well known within the art and can be used to produce a library of encoding nucleic acids which contain all possible or all desired changes and then expressing and screening the library for Vitaxin polypeptides which retain function. Such methods include, for example, codon based mutagenesis, random oligonucleotide synthesis and partially degenerate oligonucleotide synthesis.

Codon based mutagenesis is the subject matter of U.S. Pat. Nos. 5,264,563 and 5,523,388 and is advantageous for the above procedures since it allows for the production of essentially any and all desired frequencies of encoded amino acid residues at any and all particular codon positions within an oligonucleotide. Such desired frequencies include, for example, the truly random incorporation of all twenty amino acids or a specified subset thereof as well as the incorporation of a predetermined bias of one or more particular amino acids so as to incorporate a higher or lower frequency of the biased residues compared to other incorporated amino acid residues. Random oligonucleotide synthesis and partially degenerate oligonucleotide synthesis can similarly be used for producing and screening for functionally equivalent amino acid changes. However, due to the degeneracy of the genetic code, such methods will incorporate redundancies at a desired amino acid position. Random oligonucleotide synthesis is the coupling of all four nucleotides at each nucleotide position within a codon whereas partially degenerate oligonucleotide synthesis is the coupling of equal portions of all four nucleotides at the first two nucleotide positions, for example, and equal portions of two nucleotides at the third position. Both of these latter synthesis methods can be found described in, for example, Cwirla et al., *Proc. Natl. Acad. Sci. USA* 87:6378-6382, (1990) and Devlin et al., *Science* 249:404-406, (1990).

Identification of amino acids to be changed can be accomplished by those skilled in the art using current information available regarding the structure and function of antibodies as well as available and current information encompassing methods for CDR grafting procedures. For example, CDRs can be identified within the donor antibody by any or all of the criteria specified in Kabat et al., supra, Chothia et al., supra, and/or MacCallum et al., supra, and any or all non-identical amino acid residues falling outside of these CDR sequences can be changed to functionally equivalent amino acids. Using the above described methods known within the art, any or all of the non-identical amino acids can be changed either alone or in combination with amino acids at different positions to incorporate the desired number of amino acid substitutions at each of the desired positions. The Vitaxin polypeptides containing the desired substituted amino acids are then produced and screened for retention or augmentation of function compared to the unsubstituted Vitaxin polypeptides. Production of the substituted Vitaxin polypeptides can be accomplished by, for example, recombinant expression using methods known to those skilled in the art. Those Vitaxin polypeptides which exhibit retention or augmentation of function compared to unsubstituted Vitaxin are considered to contain minor modifications of the encoding nucleotide sequence which result in the functional replacement of one or more amino acids.

The functional replacement of amino acids is beneficial when producing grafted antibodies having human framework sequences since it allows for the rapid identification of equivalent amino acid residues without the need for structural information or the laborious procedures necessary to assess and identify which amino acid residues should be considered for substitution in order to successfully transfer binding function from the donor. Moreover, it eliminates the actual stepwise procedures to change and test the amino acids identified for substitution. Essentially, using the functional replacement approach described above, all non-identical amino acid residues between the donor and the human framework can be identified and substituted with any or all other possible amino acid residues at each non-identical position to produce a population of substituted polypeptides containing all possible or all desired permutations and combinations. The population of substituted polypeptides can then be screened for those substituted polypeptides which retain function. Using the codon based mutagenesis procedures described above, the generation of a library of substituted amino acid residues and the screening of functionally replaced residues has been used for the rapid production of grafted therapeutic antibodies as well as for the rapid alteration of antibody affinity. Such procedures are exemplified in, for example, Rosok et al., *J. Biol. Chem.* 271:22611-22618 (1996) and in Glaser et al., *J. Immunol.* 149:3903-3913 (1992), respectively.

The invention further provides fragments of Vitaxin heavy and light chain encoding nucleic acids wherein such fragments consist substantially of the same nucleotide or amino acid sequence as the variable region of Vitaxin heavy or light chain polypeptides. The variable region of the Vitaxin heavy chain polypeptide consists essentially of nucleotides 1-351 and of amino acid residues Gln1 to Ser117 of FIG. 1A (SEQ ID NOS:1 and 2, respectively). The variable region of the Vitaxin light chain polypeptide consists essentially of nucleotides 1-321 and of amino acid residues Glu1 to Lys107 of FIG. 1B (SEQ ID NOS:3 and 4, respectively). The termini of such variable region encoding nucleic acids is not critical so long as the intended purpose and function remains the same.

Fragments additional to the variable region nucleic acid fragments are provided as well. Such fragments include, for example, nucleic acids consisting substantially of the same nucleotide sequence as a CDR of a Vitaxin heavy or light chain polypeptide. Sequences corresponding to the Vitaxin CDRs include, for example, those regions defined by Kabat et al., supra, and/or those regions defined by Chothia et al., supra, as well as those defined by MacCallum et al., supra. The Vitaxin CDR fragments for each of the above definitions correspond to the nucleotides set forth below in Table 2. The nucleotide sequence numbering is taken from the primary sequence shown in FIGS. 1A and 1B (SEQ ID NOS:1 and 3) and conforms to the definitions previously set forth in Table 1.

TABLE 2

Vitaxin CDR Nucleotide Residues

|  | Kabat | Chothia | MacCallum |
|---|---|---|---|
| $V_H$ CDR1 | 91-105 | 76-96 | 88-105 |
| $V_H$ CDR2 | 148-198 | 157-168 | 139-177 |
| $V_H$ CDR3 | 295-318 | 298-315 | 289-315 |
| $V_L$ CDR1 | 70-102 | 76-96 | 88-108 |
| $V_L$ CDR2 | 148-168 | 148-156 | 136-165 |
| $V_L$ CDR3 | 265-291 | 271-288 | 265-288 |

Similarly, the Vitaxin CDR fragments for each of the above definitions correspond to the amino acid residues set forth below in Table 3. The amino acid residue number is taken from the primary sequence shown in FIGS. 1A and 1B (SEQ ID NOS:2 and 4) and conforms to the definitions previously set forth in Table 1.

TABLE 3

Vitaxin CDR Amino Acid Residues

|  | Kabat | Chothia | MacCallum |
|---|---|---|---|
| V$_H$ CDR1 | Ser31-Ser35 | Gly26-Tyr32 | Ser30-Ser35 |
| V$_H$ CDR2 | Lys50-Gly66 | Ser53-Gly56 | Trp47-Tyr59 |
| V$_H$ CDR3 | His99-Tyr106 | Asn100-Ala105 | Ala97-Ala105 |
| V$_L$ CDR1 | Gln24-His34 | Ser26-His32 | Ser30-Tyr36 |
| V$_L$ CDR2 | Tyr50-Ser56 | Tyr50-Ser52 | Leu46-Ile55 |
| V$_L$ CDR3 | Gln89-Thr97 | Ser91-His96 | Gln89-His96 |

Thus, the invention also provides nucleic acid fragments encoding substantially the same amino acid sequence as a CDR of a Vitaxin heavy or light chain polypeptide.

Nucleic acids encoding Vitaxin heavy and light chain polypeptides and fragments thereof are useful for a variety of diagnostic and therapeutic purposes. For example, the Vitaxin nucleic acids can be used to produce Vitaxin antibodies and functional fragments thereof having binding specificity and inhibitory activity against the integrin $\alpha_v\beta_3$. The antibody and functional fragments thereof can be used for the diagnosis or therapeutic treatment of $\alpha_v\beta_3$-mediated disease. Vitaxin and functional fragments thereof can be used, for example, to inhibit binding activity or other functional activities of $\alpha_v\beta_3$ that are necessary for progression of an $\alpha_v\beta_3$-mediated disease. Other functional activities necessary for progression of $\alpha_v\beta_3$-mediated disease include, for example, the activation of $\alpha_v\beta_3$, $\alpha_v\beta_3$-mediated signal transduction and the $\alpha_v\beta_3$-mediated prevention of apoptosis. Advantageously, however, Vitaxin comprises non-mouse framework amino acid sequences and as such is less antigenic in regard to the induction of a host immune response. The Vitaxin nucleic acids of the inventions can also be used to model functional equivalents of the encoded heavy and light chain polypeptides.

Thus, the invention provides Vitaxin heavy chain and Vitaxin light chain polypeptides or functional fragments thereof. The Vitaxin heavy chain polypeptide exhibits substantially the same amino acid sequence as that shown in FIG. 1A (SEQ ID NO:2) or functional fragment thereof whereas the Vitaxin light chain polypeptide exhibits substantially the same amino acid sequence as that shown in FIG. 1B (SEQ ID NO:4) or functional fragment thereof. Also provided is a Vitaxin antibody or functional fragment thereof. The antibody is generated from the above heavy and light chain polypeptides or functional fragments thereof and exhibits selective binding affinity to $\alpha_v\beta_3$.

The invention provides a nucleic acid encoding a heavy chain polypeptide for a LM609 grafted antibody. Also provided is a nucleic acid encoding a light chain polypeptide for a LM609 grafted antibody. The nucleic acids consist of substantially the same heavy chain variable region nucleotide sequence as that shown in FIG. 1A (SEQ ID NO:1) and substantially the same light chain variable region nucleotide sequence as that shown in FIG. 7 (SEQ ID NO:31) or a fragment thereof.

LM609 grafted antibodies, including functional fragments thereof, are non-mouse antibodies which exhibit substantially the same binding activity, binding specificity and inhibitory activity as LM609. The LM609 grafted antibody Fv fragments described herein are produced by functionally replacing the CDRs as defined by Kabat et al., hereinafter referred to as "Kabat CDRs," within human heavy and light chain variable region polypeptides with the Kabat CDRs derived from LM609. Functional replacement of the Kabat CDRs is performed by the CDR grafting methods previously described and which is the subject matter of U.S. Pat. No. 5,225,539, supra. Substitution of amino acid residues outside of the Kabat CDRs can additionally be performed to maintain or augment beneficial binding properties so long as such amino acid substitutions do not correspond to a donor amino acid at that particular position. Such substitutions allow for the modulation of binding properties without imparting any mouse sequence characteristics onto the antibody outside of the Kabat CDRs. Although the production of such antibodies is described herein with reference to LM609 grafted antibodies, the substitution of such non-donor amino acids outside of the Kabat CDRs can be utilized for the production of essentially any grafted antibody. The production of LM609 grafted antibodies is described further below in Example V.

The nucleotide sequences of the LM609 grafted antibody heavy and light chain variable regions are shown in FIGS. 1A and 7, respectively. These sequences correspond substantially to those that encode the heavy and light chain variable region polypeptides of a LM609 grafted antibody. These nucleic acids are intended to include both the sense and anti-sense strands of the LM609 grafted antibody encoding sequences. Single- and double-stranded nucleic acids are similarly included as well as non-coding portions of the nucleic acid such as introns, 5'- and 3'-untranslated regions and regulatory sequences of the gene for example.

The nucleotide and amino acid residue boundaries for a LM609 grafted antibody are identical to those previously described for Vitaxin. For example, a LM609 grafted antibody heavy chain variable region polypeptide is encoded by a nucleic acid of about 351 nucleotides in length which begins at the amino terminal Gln1 residue of the variable region through to Ser117 (FIG. 1A, SEQ ID NOS:1 and 2, respectively). The LM609 grafted antibody light chain variable region polypeptide is encoded by a nucleic acid of about 321 nucleotides in length beginning at the amino terminal Glu1 residue of the variable region through to Lys107 (FIG. 7, SEQ ID NOS:31 and 32, respectively). As with Vitaxin, minor modification of these nucleotide sequences are intended to be included as heavy and light chain variable region encoding nucleic acids and their functional fragments.

Thus, the invention also provides a nucleic acid encoding a LM609 grafted antibody heavy chain wherein the nucleic acid encodes substantially the same heavy chain variable region amino acid sequence as that shown in FIG. 1A (SEQ ID NO:2) or fragment thereof. Similarly, the invention also provides a nucleic acid encoding a LM609 grafted antibody light chain wherein the nucleic acid encodes substantially the same light chain variable region amino acid sequence as that shown in FIG. 7 (SEQ ID NO:32) or fragment thereof.

In addition to conservative substitutions of amino acids, minor modifications of the LM609 grafted antibody encoding nucleotide sequences which allow for the functional replacement of amino acids are also intended to be included within the definition of the term. Identification of amino acids to be changed can be accomplished by those skilled in the art using current information available regarding the structure and function of antibodies as well as available and current information encompassing methods for CDR grafting procedures. The substitution of functionally equivalent amino acids encoded by the LM609 grafted antibody nucleotide sequences is routine and can be accomplished by methods known to those skilled in the art. As described previously, such methods include, for example, codon based mutagenesis, random oligonucleotide synthesis and partially degenerate oligonucleotide synthesis and are beneficial when producing grafted antibodies since they allow for the rapid identification of equivalent amino acid residues without the need for structural information.

The invention further provides fragments of LM609 grafted antibody heavy and light chain encoding nucleic acids wherein such fragments consist substantially of the same nucleotide or amino acid sequence as the variable region of a LM609 grafted antibody heavy-or light chain polypeptide. As with Vitaxin, the termini of such variable region encoding nucleic acids is not critical so long as the intended purpose and function remains the same.

Fragments additional to the variable region nucleic acid fragments are provided as well and include, for example, nucleic acids consisting substantially of the same nucleotide sequence as a CDR of a LM609 grafted antibody heavy or light chain polypeptide. As with Vitaxin, sequences corresponding to the LM609 grafted antibody CDRs include, for example, those regions defined by Kabat et al., supra, Chothia et al., supra, as well as those defined by MacCallum et al., supra. The LM609 grafted antibody CDR regions will be similar to those described previously for Vitaxin. Moreover, such regions are well known and can be determined by those skilled in the art given the LM609 sequences and teachings provided herein. Thus, the invention also provides nucleic acid fragments encoding substantially the same amino acid sequence as a CDR of a LM609 grafted antibody heavy or light chain polypeptide.

As with Vitaxin, nucleic acids encoding LM609 grafted antibody heavy and light chain polypeptides and fragments thereof are useful for a variety of diagnostic and therapeutic purposes. For example, LM609 grafted antibody encoding nucleic acids can be used to produce recombinant antibodies and functional fragments thereof having binding specificity and inhibitory activity against the integrin $\alpha_v\beta_3$. The antibody and functional fragments thereof can be used for the diagnosis or therapeutic treatment of $\alpha_v\beta_3$-mediated disease. Such diseases and methods of use for anti-$\alpha_v\beta_3$ antibodies have been described previously in reference to Vitaxin and are equally applicable to the LM609 grafted antibodies described herein.

Thus, the invention provides LM609 grafted antibody heavy chain and Vitaxin light chain polypeptides or functional fragments thereof. The LM609 grafted antibody heavy chain polypeptide exhibits substantially the same amino acid sequence as that shown in FIG. 1A (SEQ ID NO:2) or functional fragment thereof whereas the LM609 grafted antibody light chain polypeptide exhibits substantially the same amino acid sequence as that shown in FIG. 7 (SEQ ID NO:32). Also provided is a LM609 grafted antibody or functional fragment thereof. The antibody is generated from the above heavy and light chain polypeptides or functional fragments thereof and exhibits selective binding affinity to $\alpha_v\beta_3$.

The invention provides a nucleic acid encoding a heavy chain polypeptide for monoclonal antibody LM609 or functional fragment thereof. Also provided is a nucleic acid encoding a light chain polypeptide for monoclonal antibody LM609 or a functional fragment thereof. The nucleic acids consist of substantially the same heavy or light chain variable region nucleotide sequences as that shown in FIGS. 2A and 2B (SEQ ID NOS:5 and 7, respectively) or a fragment thereof.

As described previously, monoclonal antibody LM609 has been shown in the art to have binding activity to the integrin $\alpha_v\beta_3$. Although specificity can in principle be generated towards essentially any target, LM609 is an integrin inhibitory antibody that exhibits substantial specificity and inhibitory activity to a single member within an integrin family. In this case, LM609 exhibits substantial specificity and inhibitory activity to the $\alpha_v\beta_3$ integrin within the $\beta_3$ family. The amino acid or nucleotide sequence of monoclonal antibody LM609 has never been previously isolated and characterized.

The isolation and characterization of LM609 encoding nucleic acids was performed by techniques known to those skilled in the art and which are described further below in the Examples. Briefly, cDNA from hybridoma LM609 was generated and used as the source for which to isolate LM609 encoding nucleic acids. Isolation was performed by first determining the N-terminal amino acid sequence for each of the heavy and light chain polypeptides and then amplifying by PCR the antibody encoding sequences from the cDNA. The 5' primers were reverse translated to correspond to the newly determined N-terminal amino acid sequences whereas the 3' primers corresponded to sequences substantially similar to antibody constant region sequences. Amplification and cloning of the products resulted in the isolation of the nucleic acids encoding heavy and light chains of LM609.

The nucleotide sequences of the LM609 heavy and light chain variable region sequences are shown in FIGS. 2A and 2B, respectively. These sequences correspond substantially to those that encode the variable region heavy and light chain polypeptides of LM609. As with the Vitaxin nucleic acids, these LM609 nucleic acids are intended to include both sense and anti-sense strands of the LM609 encoding sequences. Single- and double-stranded nucleic acids are also include as well as non-coding portions of the nucleic acid such as introns, 5'- and 3'-untranslated regions and regulatory sequences of the gene for example.

As shown in FIG. 2A, the LM609 heavy chain variable region polypeptide is encoded by a nucleic acid of about 351 nucleotides in length which begins at the amino terminal Glu1 residue of the variable region through to Ala 117. The murine LM609 antibody heavy chain has an IgG2a constant region. Shown in FIG. 2B is the LM609 light chain variable region polypeptide which is encoded by a nucleic acid of about 321 nucleotides in length which begins at the amino terminal Asp1 residue of the variable region through to Lys 107. In the functional antibody, LM609 has a kappa light chain constant region.

As with the Vitaxin nucleic acids, minor modifications of these LM609 nucleotide sequences are intended to be included as heavy and light chain LM609 encoding nucleic acids. Such minor modifications are included within the nucleic acids encoding LM609 heavy and light chain polypeptides so long as the nucleic acids or encoded polypeptides retain some or all of their function as described.

Thus, the invention also provides a nucleic acid encoding a LM609 heavy chain or functional fragment wherein the nucleic acid encodes substantially the same variable region amino acid sequence of monoclonal antibody LM609 as that shown in FIG. 2A (SEQ ID NO:6) or a fragment thereof. Similarly, the invention also provides a nucleic acid encoding a LM609 light chain or functional fragment wherein the nucleic acid encodes substantially the same variable region amino acid sequence of monoclonal antibody LM609 as that shown in FIG. 2B (SEQ ID NO:8) or a fragment thereof.

The invention further provides fragments of LM609 heavy and light chain encoding nucleic acids wherein such fragments consist substantially of the same nucleotide or amino acid sequence as the variable region of LM609 heavy or light chain polypeptides. The variable region of the LM609 heavy chain polypeptide consists essentially of nucleotides 1-351 and of amino acid residues Glu1 to Ala117 of FIG. 2A (SEQ ID NOS:5 and 6, respectively). The variable region of the LM609 light chain polypeptide consists essentially of nucleotides 1-321 and of amino acid residues Asp1 to Lys107 of FIG. 2B (SEQ ID NOS:7 and 8, respectively). The termini of such variable region encoding nucleic acids is not critical so long as the intended purpose and function remains the same. Such intended purposes and functions include, for example, use for the production of recombinant polypeptides or as hybridization probes for heavy and light chain variable region sequences.

Fragments additional to the variable region nucleic acid fragments are provided as well. Such fragments include, for example, nucleic acids consisting substantially of the same nucleotide sequence as a CDR of a LM609 heavy or light chain polypeptide. Sequences corresponding to the LM609 CDRs include, for example, those regions within the variable region which are defined by Kabat et al., supra, and/or those regions within the variable regions which are defined by Chothia et al., supra, as well as those regions defined by MacCallum et al., supra. The LM609 CDR fragments for each of the above definitions correspond to the nucleotides set forth below in Table 4. The nucleotide sequence numbering is taken from the primary sequence shown in FIGS. 2A and 2B (SEQ ID NOS:5 and 7) and conforms to the definitions previously set forth in Table 1.

TABLE 4

LM609 CDR Nucleotide Residues

|  | Kabat | Chothia | MacCallum |
|---|---|---|---|
| $V_H$ CDR1 | 91-105 | 76-96 | 88-105 |
| $V_H$ CDR2 | 148-198 | 157-168 | 139-177 |
| $V_H$ CDR3 | 295-318 | 298-315 | 288-315 |
| $V_L$ CDR1 | 70-102 | 76-96 | 88-108 |
| $V_L$ CDR2 | 148-168 | 148-156 | 136-165 |
| $V_L$ CDR3 | 265-291 | 271-288 | 265-288 |

Similarly, the LM609 CDR fragments for each of the above definitions correspond to the amino acid residues set forth below in Table 5. The amino acid residue numbering is taken from the primary sequence shown in FIGS. 2A and 2B (SEQ ID NOS:6 and 8) and conforms to the definitions set forth in Table 1.

TABLE 5

LM609 CDR Amino Acid Residues

|  | Kabat | Chothia | MacCallum |
|---|---|---|---|
| $V_H$ CDR1 | Ser31-Ser35 | Gly26-Tyr32 | Ser30-Ser35 |
| $V_H$ CDR2 | Lys50-Gly66 | Ser53-Gly56 | Trp47-Tyr59 |
| $V_H$ CDR3 | His99-Tyr106 | Asn100-Ala105 | Ala97-Ala105 |
| $V_L$ CDR1 | Gln24-His34 | Ser26-His32 | Ser30-Tyr36 |
| $V_L$ CDR2 | Tyr50-Ser56 | Tyr50-Ser52 | Leu46-Ile55 |
| $V_L$ CDR3 | Gln89-Thr97 | Ser91-His96 | Gln89-His96 |

Nucleic acids encoding LM609 heavy and light chain polypeptides and fragments thereof are useful for a variety of diagnostic and therapeutic purposes. For example, the LM609 nucleic acids can be used to produce recombinant LM609 antibodies and functional fragments thereof having binding specificity and inhibitory activity against the integrin $\alpha_v\beta_3$. The antibody and functional fragments thereof can be used to determine the presence or absence of $\alpha_v\beta_3$ in a sample to diagnose the susceptibility or occurrence of an $\alpha_v\beta_3$-mediated disease. Alternatively, the recombinant LM609 antibodies and functional fragments thereof can be used for the therapeutic treatment of $\alpha_v\beta_3$-mediated diseases or pathological state. As with Vitaxin, recombinant LM609 and functional fragments thereof can be used to inhibit the binding activity or other functional activities of $\alpha_v\beta_3$ that are necessary for progression of the $\alpha_v\beta_3$-mediated disease or pathological state.

The LM609 nucleic acids of the invention can also be used to model functional equivalents of the encoded heavy and light chain polypeptides. Such functional equivalents can include, for example, synthetic analogues or mimics of the encoded polypeptides or functional fragments thereof. A specific example would include peptide mimetics of the LM609 CDRs that retain some or substantially the same binding or inhibitory activity of LM609. Additionally, the LM609 encoding nucleic acids can be used to engineer and produce nucleic acids which encode modified forms or derivatives of the antibody LM609, its heavy and light chain polypeptides and functional fragments thereof. As described previously, such modified forms or derivatives include, for example, non-mouse antibodies, their corresponding heavy and light chain polypeptides and functional fragments thereof which exhibit substantially the same binding and inhibitory activity as LM609.

The invention also provides a method of treating an $\alpha_v\beta_3$-mediated disease. The method consists of administering an effective amount of Vitaxin, a LM609 grafted antibody or a functional fragment thereof under conditions which allow binding to $\alpha_v\beta_3$. Also provided is a method of inhibiting a function of $\alpha_v\beta_3$. The method consists of contacting $\alpha_v\beta_3$ with Vitaxin, a LM609 grafted antibody or a functional fragment thereof under conditions which allow binding to $\alpha_v\beta_3$.

As described previously, Vitaxin and LM609 grafted antibodies are monoclonal antibodies which exhibit essentially all of the binding characteristics as does its parental CDR-donor antibody LM609. These characteristics include, for example, significant binding specificity and affinity for the integrin $\alpha_v\beta_3$. The Examples below demonstrate these binding properties and further show that the binding of such antibodies to $\alpha_v\beta_3$ inhibits $\alpha_v\beta_3$ ligand binding and function. Thus, Vitaxin and LM609 grafted antibodies are useful for a large variety of diagnostic and therapeutic purposes directed to the inhibition of $\alpha_v\beta_3$ function.

The integrin $\alpha_v\beta_3$ functions in numerous cell adhesion and migration associated events. As such, the dysfunction or dysregulation of this integrin, its function, or of cells expressing this integrin, is associated with a large number of diseases and pathological conditions. The inhibition $\alpha_v\beta_3$ binding or function can therefore be used to treat or reduce the severity of such $\alpha_v\beta_3$-mediated pathological conditions. Described below are examples of several pathological conditions mediated by $\alpha_v\beta_3$, since the inhibition of at least this integrin reduces the severity of the condition. These examples are intended to be representative and as such are not inclusive of all $\alpha_v\beta_3$-mediated diseases. For example, there are numerous pathological conditions additional to those discussed below which exhibit the dysregulation of $\alpha_v\beta_3$ binding, function or the dysregulation of cells expressing this integrin and in which the pathological condition can be reduced, or will be found to be reduced, by inhibiting the binding $\alpha_v\beta_3$. Such pathological conditions which exhibit this criteria, are intended to be included within the definition of the term as used herein.

Angiogenesis, or neovascularization, is the process where new blood vessels form from pre-existing vessels within a tissue. As described further below, this process is mediated by endothelial cells expressing $\alpha_v\beta_3$ and inhibition of at least this integrin, inhibits new vessel growth. There are a variety of pathological conditions that require new blood vessel formation or tissue neovascularization and inhibition of this process inhibits the pathological condition. As such, pathological conditions that require neovascularization for growth or maintenance are considered to be $\alpha_v\beta_3$-mediated diseases. The extent of treatment, or reduction in severity, of these diseases will therefore depend on the extent of inhibition of neovascularization. These $\alpha_v\beta_3$-mediated diseases include, for example, inflammatory disorders such as immune and non-immune inflammation, chronic articular rheumatism, psoriasis, disorders associated with inappropriate or inopportune invasion of vessels such as diabetic retinopathy, neovascular glaucoma and capillary proliferation in atherosclerotic plaques as well as cancer disorders. Such cancer disorders can include, for example, solid tumors, tumor metastasis, angiofibromas, retrolental, fibroplasia, hemangiomas, Kaposi's sarcoma and other cancers which require neovascularization to support tumor growth. Additional diseases which are considered angiogenic include psoriasis and rheumatoid arthritis as well as retinal diseases such as macular degeneration. Diseases other than those requiring new blood vessels which are $\alpha_v\beta_3$-mediated diseases include, for example, restenosis and osteoporosis.

Treatment of the $\alpha_v\beta_3$-mediated diseases can be performed by administering an effective amount of Vitaxin, a LM609 grafted antibody or a functional fragment thereof so as to bind to $\alpha_v\beta_3$ and inhibit its function. Administration can be performed using a variety of methods known in the art. The choice of method will depend on the specific $\alpha_v\beta_3$-mediated disease and can include, for example, the in vivo, in situ and ex vivo administration of Vitaxin, a LM609 grafted antibody or functional fragment thereof, to cells, tissues, organs, and organisms. Moreover, such antibodies or functional fragments can be administered to an individual exhibiting or at risk of exhibiting an $\alpha_v\beta_3$-mediated disease. Definite clinical diagnosis of an $\alpha_v\beta_3$-mediated disease warrants the administration of Vitaxin, a LM609 grafted antibody or a functional fragment thereof. Prophylactic applications are warranted in diseases where the $\alpha_v\beta_3$-mediated disease mechanisms precede the onset of overt clinical disease. Thus, individuals with familial history of disease and predicted to be at risk by reliable prognostic indicators can be treated prophylactically to interdict $\alpha_v\beta_3$-mediated mechanisms prior to their onset.

Vitaxin, a LM609 grafted antibody or functional fragments thereof can be administered in a variety of formulations and pharmaceutically acceptable media for the effective treatment or reduction in the severity of an $\alpha_v\beta_3$-mediated disease. Such formulations and pharmaceutically acceptable medias are well known to those skilled in the art. Additionally, Vitaxin, a LM609 grafted antibody or functional fragments thereof can be administered with other compositions which can enhance or supplement the treatment or reduction in severity of an $\alpha_v\beta_3$-mediated disease. For example, the coadministration of Vitaxin or a LM609 grafted antibody to inhibit tumor-induced neovascularization and a chemotherapeutic drug to directly inhibit tumor growth is one specific case where the administration of other compositions can enhance or supplement the treatment of an $\alpha_v\beta_3$-mediated disease.

Vitaxin, a LM609 grafted antibody or functional fragments are administered by conventional methods, in dosages which are sufficient to cause the inhibition of $\alpha_v\beta_3$ integrin binding at the sight of the pathology. Inhibition can be measured by a variety of methods known in the art such as in situ immunohistochemistry for the prevalence of $\alpha_v\beta_3$ containing cells at the site of the pathology as well as include, for example, the observed reduction in the severity of the symptoms of the $\alpha_v\beta_3$-mediated disease.

In vivo modes of administration can include intraperitoneal, intravenous and subcutaneous administration of Vitaxin, a LM609 grafted antibody or a functional fragment thereof. Dosages for antibody therapeutics are known or can be routinely determined by those skilled in the art. For example, such dosages are typically administered so as to achieve a plasma concentration from about 0.01 µg/ml to about 100 µg/ml, preferably about 1-5 µg/ml and more preferably about 5 µg/ml. In terms of amount per body weight, these dosages typically correspond to about 0.1-300 mg/kg, preferably about 0.2-200 mg/kg and more preferably about 0.5-20 mg/kg. Depending on the need, dosages can be administered once or multiple times over the course of the treatment. Generally, the dosage will vary with the age, condition, sex and extent of the $\alpha_v\beta_3$-mediated pathology of the subject and should not be so high as to cause adverse side effects. Moreover, dosages can also be modulated by the physician during the course of the treatment to either enhance the treatment or reduce the potential development of side effects. Such procedures are known and routinely performed by those skilled in the art.

The specificity and inhibitory activity of Vitaxin, LM609 grafted antibodies and functional fragments thereof allow for the therapeutic treatment of numerous $\alpha_v\beta_3$-mediated diseases. Such diseases include, for example, pathological conditions requiring neovascularization such as tumor growth, and psoriasis as well as those directly mediated by $\alpha_v\beta_3$ such as restenosis and osteoporosis. Thus, the invention provides methods as well as Vitaxin and LM609 grafted antibody containing compositions for the treatment of such diseases.

Throughout this application various publications are referenced within parentheses. The disclosures of these publications in their entireties are hereby incorporated by reference in this application in order to more fully describe the state of the art to which this invention pertains.

It is understood that modifications which do not substantially affect the activity of the various embodiments of this invention are also included within the definition of the invention provided herein. Accordingly, the following examples are intended to illustrate but not limit the present invention.

EXAMPLE I

Isolation And Characterization of LM609 Encoding Nucleic Acids

This Example shows the cloning and sequence determination of LM609 encoding nucleic acids.

LM609 is directed against the human vitronectin receptor, integrin $\alpha_v\beta_3$. $\alpha_v\beta_3$ is highly upregulated in melanoma, glioblastoma, and mammary carcinoma and plays a role in the proliferation of M21 melanoma cells both in vitro and in vivo. $\alpha_v\beta_3$ also plays a role in angiogenesis, restenosis and the formation of granulation tissue in cutaneous wounds. LM609 has been shown to inhibit the adhesion of M21 cells to vitronectin as well as prevent proliferation of M21 cells in vitro. Thus, grafting of LM609 could result in a clinically valuable therapeutic agent.

cDNA Synthesis of LM609 Variable Regions: For cDNA synthesis, total RNA was prepared from $10^8$ LM609 hybridoma cells using a modification of the method described by Chomczynski and Sacchi (Chomczynski and Sacchi, *Analyt. Biochem.* 162:156 (1987)). LM609 variable (V) region genes were cloned by reverse transcription-polymerase chain reaction (RT-PCR) and cDNA was synthesized using BRL Superscript kit. Briefly, 5 µg of total cellular RNA, 650 ng oligo dT and $H_2O$ were brought to a total volume of 55 µl. The sample was heated to 70° C. for 10 min and chilled on ice. Reaction buffer was added and the mixture brought to 10 mM DTT and 1 mM dNTPs and heated at 37° C. for 2 minutes. 5 µl (1000 units) reverse transcriptase was added and incubated at 37° C. for 1 hour and then chilled on ice.

All oligonucleotides were synthesized by β-cyanoethyl phosphoramidite chemistry on an ABI 394 DNA synthesizer. Oligonucleotides used for PCR amplification and routine site-directed mutagenesis were purified using oligonucleotide purification cartridges (Applied Biosystems, Foster City, Calif.). Forward PCR primers were designed from N-terminal protein sequence data generated from purified LM609 antibody. The forward PCR primers contained sequences coding for the first six amino acids in each antibody variable chain (protein sequenced at San Diego State University). The sequence of the light chain forward PCR primer (997) was 5'-GCC CAA CCA GCC ATG GCC GAT ATT GTG CTA ACT CAG-3' (SEQ ID NO:19) whereas the light chain reverse PCR primer (734) was 5'-AC AGT TGG TGC AGC ATC AGC-3' (SEQ ID NO:20) used. This reverse primer corresponds to mouse light chain kappa amino acid residues 109-115. The sequence of the heavy chain forward PCR primer (998) was 5'-ACC CCT GTG GCA AAA GCC GAA GTG CAG CTG GTG GAG-3' (SEQ ID NO:21). Heavy chain reverse PCR primer 733: 5'-GA TGG GGG TGT CGT TTT GGC-3' SEQ ID NO:22). The PCR primers also contain regions of homology with specific sequences within the immunoexpression vector.

$V_L$ and $V_H$ chains were amplified in two separate 50 μl reaction mixtures containing 2 μl of the cDNA-RNA heteroduplex, 66.6 mM Tris-HCl pH 8.8, 1.5 mM $MgCl_2$, 0.2 mM of each four dNTPs, 10 mM 2-mercaptoethanol, 0.25 units Taq polymerase (Boehringer-Mannheim, Indianapolis, Ind.) and 50 pmoles each of primers 997 and 734 and 998 and 733, respectively. The mixtures were overlaid with mineral oil and cycled for two rounds of PCR with each cycle consisting of 30 seconds at 94° C. (denature), 30 seconds at 50° C. (anneal), and 30 seconds at 72° C. (synthesis). This reaction was immediately followed by 30 cycles of PCR consisting of 30 seconds at 94° C. (denature), 30 seconds at 55° C. (anneal), and 30 seconds at 72° C. (synthesis) followed by a final synthesis reaction for 5 minutes at 72° C. The reaction products were pooled, extracted with $CHCl_3$ and ethanol precipitated.

Amplified products were resuspended in 20 μl TE buffer (10 mM Tris-HCl, 1 mM EDTA, pH 8.0) and electrophoresed on a 5% polyacrylamide gel. Bands migrating at expected molecular weights of $V_H$ and $V_L$ were excised, chemically eluted from the gel slice, extracted with organic solvents and ethanol precipitated.

Cloning of amplified $V_H$ and $V_L$ genes into M13 phage immunoexpression vector: The amplified V region gene products were sequentially cloned into the phage immunoexpression vector by hybridization mutagenesis (Near, R. *Biotechniques* 12:88 (1992); Yelton et al., *J. Immunol.* 155:1994-2003 (1995)). Introduction of the amplified $V_L$ and $V_H$ sequences by hybridization mutagenesis positions the antibody sequences in frame with the regulatory elements contained in the M13 vector required for efficient Fab expression. One advantage of this technique is that no restriction endonuclease sites need to be incorporated into the $V_L$ or $V_H$ gene sequences for cloning as is done with conventional DNA ligation methods.

To perform the cloning, 400 ng each of the double-stranded amplified products were first phosphorylated with polynucleotide kinase. 100 ng of the phosphorylated LM609 $V_L$ product was mixed with 250 ng of uridinylated BS11 phage immunoexpression vector, denatured by heating to 90° C. and annealed by gradual cooling to room temperature. BS11 is an M13 immunoexpression vector derived from M13 IX and encodes $CH_1$ of murine IgG1 and murine kappa light chain constant domain (Huse, W. D. In: Antibody Engineering: A Practical Guide, C. A. K. Borrebaeck, ed. W. H. Freeman and Co., Publishers, New York, pp. 103-120 (1991)). Nucleotide sequences included in the PCR amplification primers anneal to complementary sequences present in the single-stranded BS11 vector. The annealed mixture was fully converted to a double-stranded molecule with T4 DNA polymerase plus dNTPs and ligated with T4 ligase. 1 μl of the mutagenesis reaction was electroporated into *E. coli* strain DH10B, titered onto a lawn of XL-1 *E. coli* and incubated until plaques formed. Plaque lift assays were performed as described using goat anti-murine kappa chain antibody conjugated to alkaline phosphatase (Yelton et al, supra; Huse, W. D., supra). Fifteen murine light chain positive M13 phage clones were isolated, pooled and used to prepare uridinylated vector to serve as template for hybridization mutagenesis with the PCR amplified LM609 $V_H$ product.

Clones expressing functional murine LM609 Fab were identified by binding to purified $α_vβ_3$ by ELISA. Briefly, Immulon II ELISA plates were coated overnight with 1 μg/ml (100 ng/well) $α_vβ_3$ and nonspecific sites blocked for two hours at 27° C. Soluble Fabs were prepared by isolating periplasmic fractions of cultures of *E. coli* strain MK30-3 (Boehringer Mannheim Co.) infected with the Fab expressing M13 phage clones. Periplasm fractions were mixed with binding buffer 100 mM NaCl, 50 mM Tris pH 7.4, 2mM $CaCl_2$, 1 mM $MgCl_2$, 1 mM $MnCl_2$, 0.02% $NaN_3$, 1 mg/ml BSA and incubated with immobilized $α_vβ_3$ for two hours at 27° C. Plates were washed with binding buffer and bound Fab detected with goat anti-murine kappa chain antibody conjugated to alkaline phosphatase. Four $α_vβ_3$ reactive clones were identified: muLM609M13 12, 29, 31 and 69. MuLM609M13 12 and 29 gave the strongest signals in the ELISA assay. DNA sequence analysis showed that clones muLM609M13 12, 31 and 69 all had identical light chain sequence and confirmed the previously determined N-terminal amino acid sequence of purified LM609 light chain polypeptide. All four clones had identical $V_H$ DNA sequence and also confirmed the previously determined N-terminal amino acid sequence of purified LM609 heavy chain polypeptide.

To further characterize the binding activity of each clone, soluble Fab fractions were prepared from 50 ml cultures of *E. coli* strain MK30-3 infected with clones 12 and 29 and evaluated for binding to $α_vβ_3$ in a competitive ELISA with LM609 IgG. The results of this ELISA are shown in FIG. 3. Clone muLM609M13 12 was found to inhibit LM609 IgG binding (at LM609 IgG concentrations of 1 ng/ml and 5 ng/ml) to $α_vβ_3$ in a concentration dependent manner at periplasm titers ranging from neat to 1:80. Clone muLM609M13 12 was plaque purified and both the V region heavy and light chain DNA sequences again determined. Complete DNA sequence of the final clone, muLM609M13 12-5, is shown in FIGS. 2A and 2B.

EXAMPLE II

Construction of Vitaxin: A CDR Grafted LM609 Functional Fragment

One goal of grafting antibodies is to preserve antibody specificity and affinity when substituting non-human CDRs into a human antibody framework. Another goal is to minimize the introduction of foreign amino acid sequences so as to reduce the possible antigenicity with a human host. This Example describes procedures for accomplishing both of these goals by producing libraries of grafted antibodies which represent all possible members which exhibit the highest affinities for the desired antigen.

The above library was constructed in *E. coli* wherein the possible CDR and framework changes were incorporated using codon-based mutagenesis (Kristensson et al., In: Vaccines 95. Cold Spring Harbor Laboratory Press. Cold Spring Harbor, N.Y. (1995); Rosok et al., *J. Biol. Chem*. (271:22611-22613 (1996)). Using these procedures, a library was constructed and a functionally active humanized anti-$\alpha_v\beta_3$-inhibitory antibody was identified.

For the construction of one grafted form of LM609, human framework sequences showing the highest degree of identity to the murine LM609 V region gene sequences were selected for receiving the LM609 CDRs. Human heavy chain V region M72 'CL (HHC30Q, HC Subgroup 3, Kabat et al., supra) had 88% identity to frameworks 1, 2 and 3 of LM609 heavy chain and human light chain V region LS1 'CL (HKL312, Kappa subgroup 3, Kabat et al., supra) had 79% identity to frameworks 1, 2 and 3 of LM609 light chain. Murine LM609 CDR sequences, as defined by Kabat et al., supra were grafted onto the human frameworks. Residues predicted to be buried that might affect the structure and therefore the binding properties of the original murine combining site were taken into consideration when designing possible changes (Singer et al., supra; Padlan, E. A. *Mol. Immunol*. 28:489-498 (1991)). This analysis of framework residues considered to be important for preserving the specificity and affinity of the combining site revealed only a few differences. For example, in the heavy chain sequence, the predicted buried residues displayed 100% identity. Of particular note is that Arg16 in human heavy chain V region M72 'CL is a relatively uncommon residue among human chains. However, this residue was also found to be present in LM609 $V_H$ and therefore was retained. Similarly, Arg19 in LM609 is a relatively rare residue among murine heavy chains but it is found to occur in M72 'CL and was therefore retained. In the light chain sequences, two nonidentical buried residues were identified between LM609 and LS1 'CL framework regions at positions 49 and 87. These two positions were therefore incorporated into the grafted antibody library as both human and murine alternatives.

Full-length grafted V region genes were synthesized by PCR using long overlapping oligonucleotides. Light chain oligonucleotides containing mixed amino acid residues at positions 49 and 87 were synthesized as described in Glaser et. al. (*J. Immunol*. 149:3903-3913 (1992)) and as illustrated in the oligonucleotides represented as $V_L$ oligo3 and $V_L$ oligo4. (SEQ ID NOS:16 and 17, respectively). All long oligonucleotides were gel purified.

Grafted LM609 heavy and light chain V regions were constructed by mixing 5 overlapping oligonucleotides at equimolar concentrations, in the presence of annealing PCR primers. The heavy chain oligonucleotides map to the following nucleotide positions: $V_H$ oligonucleotide 1 ($V_H$ oligo1), nucleotides (nt) 1-84; (SEQ ID NO:9); $V_H$ oligo2, nt 70-153, (SEQ ID NO:10); $V_H$ oligo3, nt 138-225 (SEQ ID NO:11); $V_H$ oligo4, nt 211-291 (SEQ ID NO:12); $V_H$ oligo5, nt 277-351 (SEQ ID NO:13). Similarly, the Vitaxin light chain oligonucleotides map to the following nucleotide positions: $V_L$ oligonucleotide 1 ($V_L$ oligo1), nucleotides (nt) 1-87; (SEQ ID NO:14); $V_L$ oligo2, nt 73-144, (SEQ ID NO:15); $V_L$ oligo3, nt 130-213 (SEQ ID NO:16); $V_L$ oligo4, nt 199-279 (SEQ ID NO:17); $V_L$ oligo5, nt 265-321 (SEQ ID NO:18). Codon positions 49 and 87 in $V_L$ oligo3, and $V_L$ oligo4 represent the randomized codons. The annealing primers contained at least 18 nucleotide residues complementary to vector sequences for efficient annealing of the amplified V region product to the single-stranded vector. The annealed mixture was fully converted to a double-stranded molecule with T4 DNA polymerase plus dNTPs and ligated with T4 ligase.

To generate the library, a portion of the mutagenesis reaction (1 μl) was electroporated into *E. coli* strain DH10B (BRL), titered onto a lawn of XL-1 (Stratagene, Inc.) and incubated until plaques formed. Replica filter lifts were prepared and plaques containing $V_H$ gene sequences were screened either by hybridization with a digoxigenin-labeled oligonucleotide complementary to LM609 heavy chain CDR 2 sequences or reactivity with 7F11-alkaline phosphatase conjugate, a monoclonal antibody raised against the decapeptide sequence Tyr Pro Tyr Asp Val Pro Asp Tyr Ala Ser (SEQ ID NO:28) appended to the carboxy terminus of the vector $CH_1$ domain (Biosite, Inc., San Diego, Calif.). Fifty clones that were double-positive were pooled and used to prepare uridinylated template for hybridization mutagenesis with the amplified grafted LM609 $V_L$ product.

The mutagenesis reaction was performed as described above with the $V_H$ oligonucleotides except that the $V_L$ oligonucleotides 1 to 5 were employed (SEQ ID NOS:14 to 18, respectively). The reaction was electroporated into *E. coli* strain DH10B and filter lifts probed with either goat anti-human kappa chain antibody conjugated to alkaline phosphatase or a goat anti-human Fab antibody using an alkaline phosphatase conjugated rabbit anti-goat secondary reagent for detection. Positive clones co-expressing both $V_H$ and $V_L$ gene sequences were selected (160 total) and used to infect *E. coli* strain MK30-3 for preparing soluble Fab fragments.

The soluble Fab fragments were screened for binding to $\alpha_v\beta_3$ in an ELISA assay. Four clones that were shown from the ELISA to strongly bind $\alpha_v\beta_3$ were identified and further characterized. These clones were termed huLM609M13-34, 54, 55 and 145. All four clones were plaque purified and three independent subclones from each clone was used to prepare Fab fragments for additional binding analysis to $\alpha_v\beta_3$ by ELISA.

In this additional ELISA, duplicate plates were coated with $\alpha_v\beta_3$ ligand and incubated with the huLM609 periplasmic samples. In one plate, bound huLM609 Fab was detected with goat anti-human kappa chain antibody conjugated to alkaline phosphatase and in the other plate bound huLM609 Fab was detected with 7F11-alkaline phosphatase conjugate, the monoclonal antibody recognizing the decapeptide tag. Subclones huLM609M13-34-1, 2 and 3 and huLM609M13-145-1, 2 and 3 all yielded double positive signals indicating that the Fabs contain functional $V_H$ and $V_L$ polypeptides. These results were confirmed in an ELISA assay on M21 cells, a cell line that expresses the integrin $\alpha_v\beta_3$.

DNA sequence analysis of subclones huLM609M13-34-3 and huLM609M13-145-3 revealed mutations introduced into the library by errors due to oligonucleotide synthesis or by errors arising during PCR amplification. These mutations were corrected in clone huLM609M13-34-3 by site-directed mutagenesis. In the light chain sequence the following corrections were made: His36 to Tyr36 and Lys18 to Arg18. In the heavy chain sequence the following corrections were made: Glu1 to Gln1, Asn3 to Gln3, Leu11 to Val11. Additionally, during the construction of LM609 grafted molecules, residue 28 from the heavy chain was considered to be a non-critical framework residue and the human residue (Thr28) was retained. Subsequently, however, it has been determined that residue 28 can be considered part of the CDR. Therefore, residue 28 was converted to the corresponding mouse residue at that position (Ala28) using site directed mutagenesis with the oligonucleotide 5'-GCT ACT GAA GGC GAA TCC AGA G-3' (SEQ ID NO:29). This change was later determined to not provide benefit over the human framework threonine at this site, and the threonine was retained. The final grafted LM609 clone was designated huLM609M13 1135-4 and is termed herein Vitaxin. The DNA sequence of clone Vitaxin is shown in FIGS. 2A and 2B.

EXAMPLE III

Functional Characterization of Vitaxin

This Example shows the characterization of Vitaxin's binding specificity, affinity and functional activity in a number of in vitro binding and cell adhesion assays.

The binding specificity of Vitaxin for the integrin $\alpha_v\beta_3$ was initially assessed by measuring binding to $\alpha_v\beta_3$ and its cross-reactivity to other $\alpha_v$- or $\beta_3$-containing integrins. Specifically, binding specificity was assessed by measuring binding to $\alpha_{IIb}\beta_3$, the major integrin expressed on platelets, and to $\alpha_v\beta_5$, an integrin found prevalent on endothelial cells and connective tissue cell types.

Briefly, to determine crossreactivity, integrins were coated onto an ELISA plate and a series of antibody dilutions were measured for Vitaxin binding activity against $\alpha_v\beta_3$ and the other integrins. The integrins $\alpha_v\beta_3$ and $\alpha_v\beta_5$ were isolated by affinity chromatography as described by Cheresh (1987), supra, and Cheresh and Spiro (1987), supra. $\alpha_{IIb}\beta_3$ was purchased from CalBiochem. Briefly, an LM609 affinity column (Cheresh and Spiro (1987), supra) was used to isolate $\alpha_v\beta_3$ from an octylglucoside human placental lysate, whereas an anti-$\alpha_v$ affinity column was used to isolate $\alpha_v\beta_5$ from the $\alpha_v\beta_3$-depleted column flow through. Antibody binding activity was assessed by ELISA using a goat anti-human IgG-alkaline phosphatase conjugate. As a control, a purified human IgG$_1$ antibody was used since Vitaxin contains a human IgG$_1$ backbone.

Figure 4A:
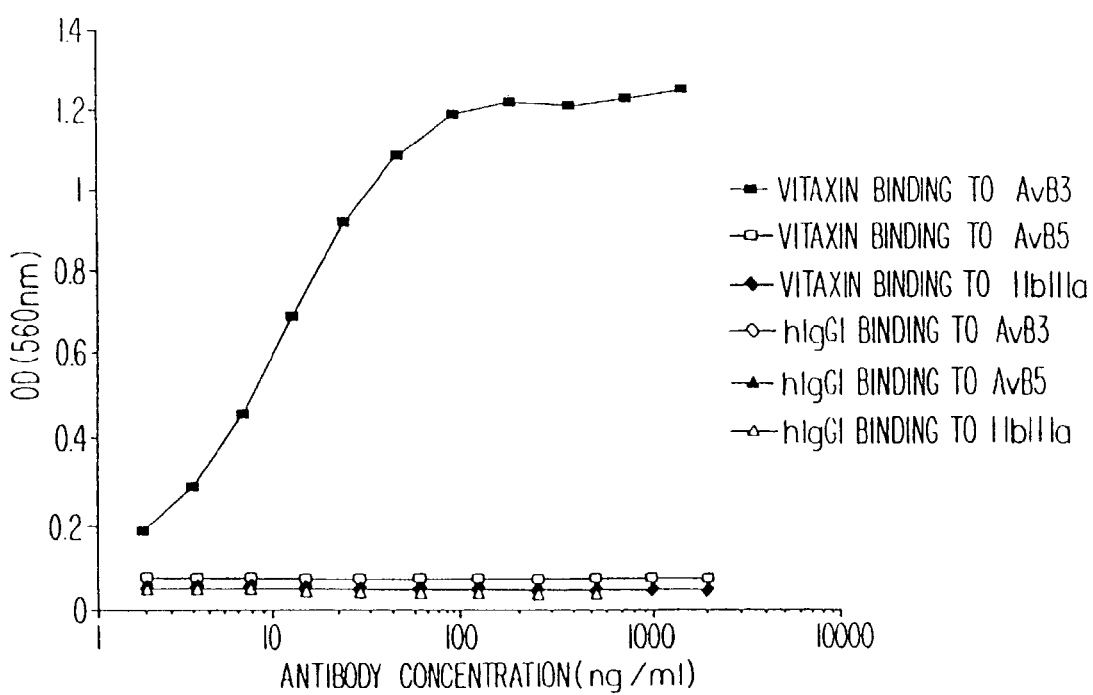
FIG. 4A shows specific binding of Vitaxin to the integrin $\alpha_v\beta_3$ compared to integrins $\alpha_{IIb}\beta_3$ and $\alpha_v\beta_5$.

The results of this assay are shown in FIG. 4A and reveal that Vitaxin specifically binds to $\alpha_v\beta_3$ with high affinity. There was no detectable binding to the other $\alpha_v$- or $\beta_3$-containing integrins at antibody concentrations over 1.0 mg/ml.

In a further series of binding studies, the binding affinity and specificity was assessed in a competitive binding assay with the parental LM609 antibody against $\alpha_v\beta_3$. Competitive binding was measured in an ELISA assay as described above with LM609 being the labeled antibody. Binding of LM609 was determined in the presence of increasing concentrations of Vitaxin competitor. Alternatively, the control competitor antibody was again a human IgG$_1$.

Figure 4B:
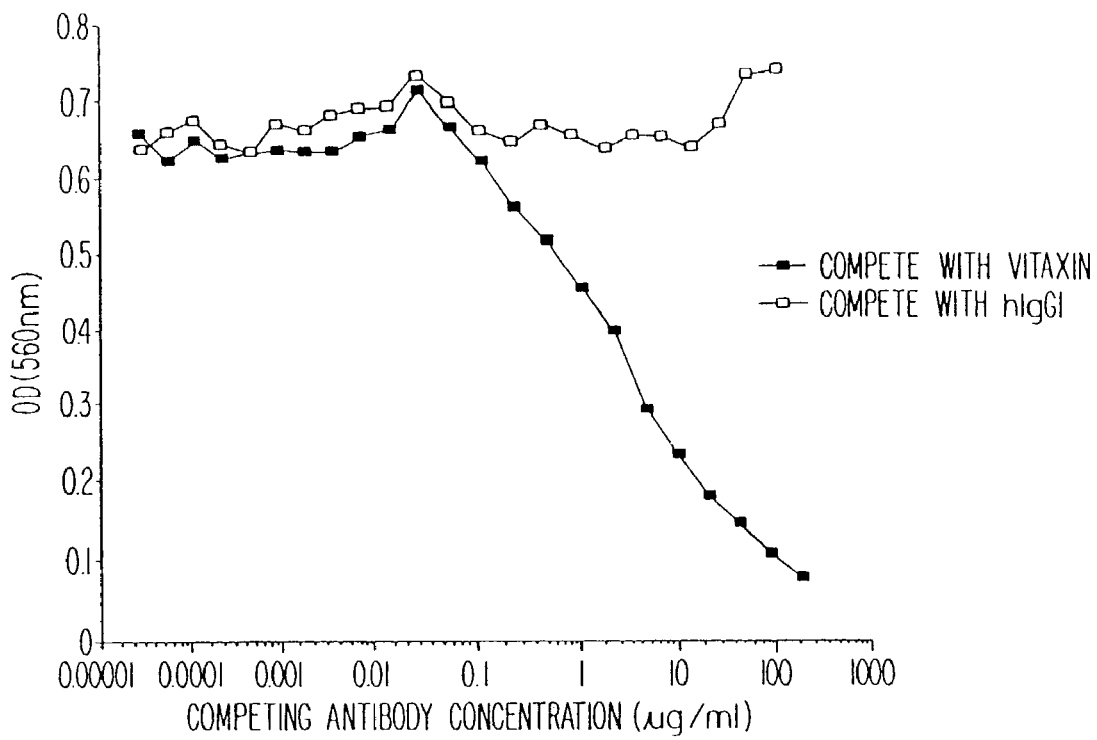
FIG. 4B shows the competitive inhibition of LM609 binding to $\alpha_v\beta_3$ by Vitaxin.

The results of this competition are presented in FIG. 4B and show that specific inhibition of LM609 binding can be observed at Vitaxin concentrations of over 0.1 µg/ml. Almost complete inhibition is observed at Vitaxin concentrations greater than 100 µg/ml. This level of competitive inhibition indicates that the parental monoclonal antibody LM609 and the grafted version Vitaxin exhibit essentially identical specificity.

Binding affinity and specificity were also assessed by measuring the inhibitory activity of Vitaxin on $\alpha_v\beta_3$ binding to fibrinogen. For these studies, $\alpha_v\beta_3$ was plated onto ELISA plates as described above for the Vitaxin/$\alpha_v\beta_3$ binding studies. Inhibitory activity of Vitaxin was determined by measuring the amount of bound biotinylated fibrinogen in the presence of increasing concentrations of Vitaxin or control antibody. Briefly, fibrinogen was purchased from CalBiochem and biotinylated with N-hydroxysuccinimidobiotin as described by the manufacturer (Pierce Life Science and Analytical Research). Streptavidin alkaline phosphatase was used to detect the bound fibrinogen.

Figure 4C:
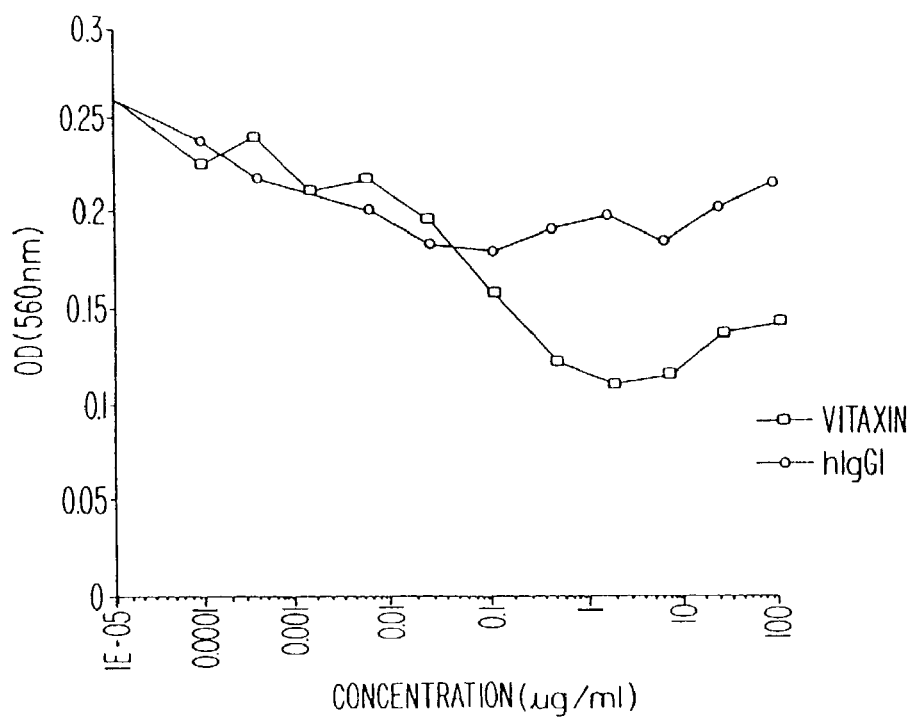
FIG. 4C shows the competitive inhibition of fibrinogen binding to $\alpha_v\beta_3$ by Vitaxin.

The results of this assay are presented in FIG. 4C and reveal a specific binding inhibition at Vitaxin concentrations higher than about 0.1 µg/ml. These results, combined with those presented above showing specific binding of Vitaxin to $\alpha_v\beta_3$ and competitive inhibition of LM609, demonstrate that Vitaxin maintains essentially all of the binding characteristics and specificity exhibited by the parental murine monoclonal antibody LM609. Described below are additional functional studies which corroborate these conclusions based on in vitro binding assays.

Additional functional studies were performed to further assess the specificity of Vitaxin binding. These studies were directed to the inhibition of integrin $\alpha_v\beta_3$ binding in cell adhesion assays. Endothelial cell adhesion events are an important component in the angiogenic process and inhibition of $\alpha_v\beta_3$ is known to reduce the neovascularization of tumors and thereby reduce the rate of tumor growth. The inhibition of $\alpha_v\beta_3$-mediated cell attachment by Vitaxin in these assays is indicative of the inhibitory activity expected when this antibody is used in situ or in vivo.

Briefly, $\alpha_v\beta_3$-positive M21 melanoma cells grown in RPMI containing 10% FBS were used for these cell binding assays. Cells were released from the culture dish by trypsinization and re-suspended in adhesion buffer at a concentration of 4×10$^5$ cells/ml (see below) Vitaxin, LM609 or purified human IgG$_1$ (control antibody), were diluted to the desired concentration in 250 µl adhesion buffer (10 mM Hepes, 2 mM MgCl$_2$, 2 mM CaCl$_2$, 0.2 mM MnCl$_2$, and 1% BSA in Hepes buffered saline at pH 7.4) and added to wells of a 48-well plate precoated with fibrinogen. The fibrinogen was isolated as described above. Each well was coated with 200 µl fibrinogen at a concentration of 10 µg/ml for 1 hour at 37° C. For the assay, an equal volume of cells (250 µl) containing Vitaxin, LM609 or isotype matched control antibody was added to each of the wells, mixed by gentle shaking and incubated for 20 minutes at 37° C. Unbound cells were removed by washing with adhesion buffer until no cells remained in control wells coated with BSA alone. Bound cells were visualized by staining with crystal violet which was subsequently extracted with 100 µl acetic acid (10%) and quantitated by determining the absorbance of the solubilized dye at 560 nm.

Figure 5A:
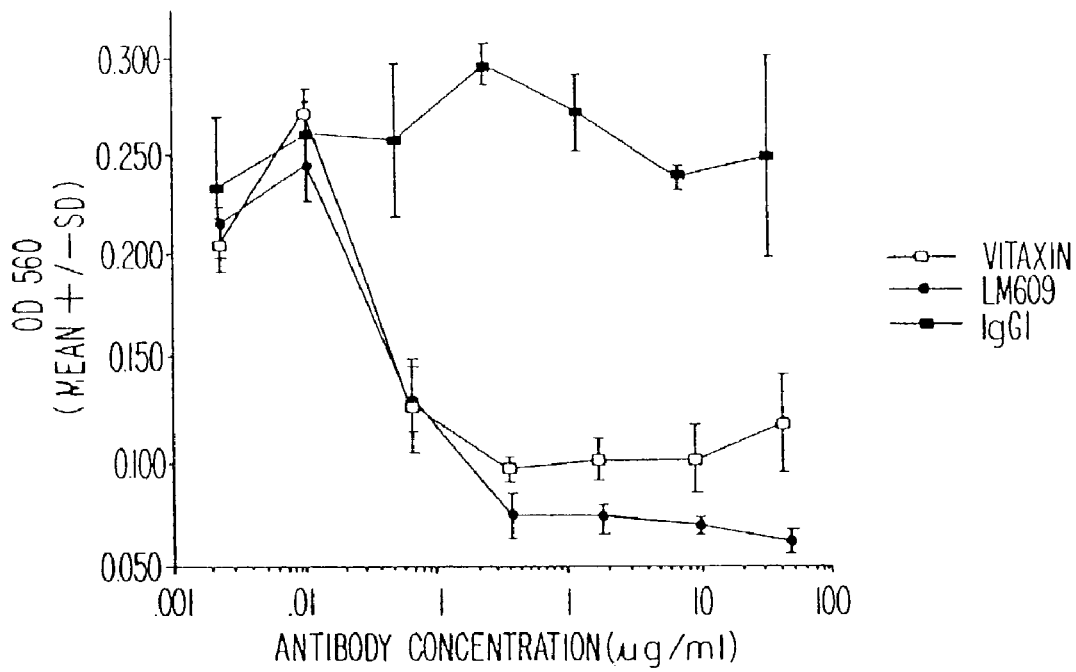
FIG. 5 shows the inhibition of $\alpha_v\beta_3$-mediated cell attachment (5A) and migration (5B) by Vitaxin.
Figure 5B:
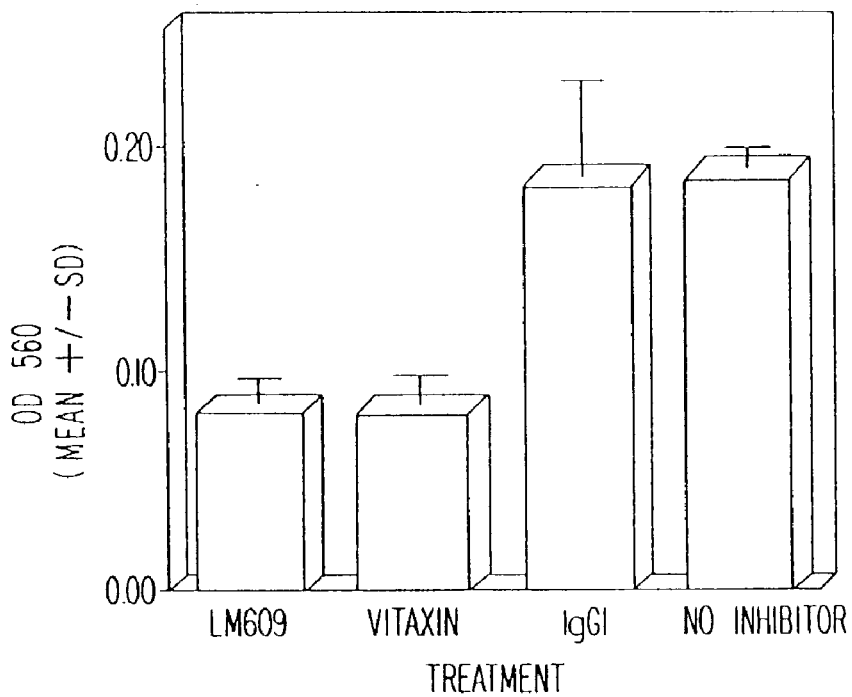

The results of this assay are shown in FIG. 5A and reveal that both Vitaxin and parental antibody LM609 inhibit M21 cell adhesion to fibrinogen over the same concentration range. The inhibitory concentration for 50% maximal adhesion was calculated to be about 50 ng/ml. Specificity of Vitaxin was shown by the lack of inhibition observed by the control IgG$_1$ antibody.

In addition to the above cell adhesion results, the inhibitory activity of Vitaxin was also tested in an endothelial cell migration assay. In this regard, the transwell cell migration assay was used to assess the ability of Vitaxin to inhibit endothelial cell migration (Choi et al., *J. Vascular Surg.*, 19:125-134 (1994) and Leavesly et al., *J. Cell Biol*, 121:163-170 (1993)).

Briefly, human umbilical vein endothelial cells in log phase and at low passage number were harvested by gentle trypsinization, washed and resuspended at a concentration of 2×10$^6$ cells/ml in 37° C. HBS containing 1% BSA (20 mM HEPES, 150 mM NaCl, 1.8 mM CaCl$_2$, 1.8 mM MgCl$_2$, 5 mM KCl, and 5 mM glucose, pH 7.4). Antibodies (Vitaxin, LM609, and IgG$_1$ control) were diluted to 10 µg/ml from stock solutions. Antibodies were added to cells in a 1:1 dilution (final concentration of antibodies=5 µg/ml; final concentration of cells=1×10$^6$ cells/ml) and incubated on ice for 10-30 minutes. The cell/antibody suspensions (200 µl to each compartment) were then added to the upper compartments of a Transwell cell culture chamber (Corning Costar), the lower compartments of which had been coated with 0.5 ml of 10 µg/ml vitronectin (in HBS). Vitronectin serves as the chemoattractant for the endothelial cells. The chambers were placed at 37° C. for 4 hours to allow cell migration to occur.

Visualization of cell migration was performed by first removing the remaining cells in the upper compartment with a cotton swab. Cells that had migrated to the lower side of the insert were stained with crystal violet for 30 minutes, followed by solubilization in acetic acid and the absorbance of the dye was measured at a wavelength of 550 nm. The amount of absorbance is directly proportional to the number of cells that have migrated from the upper to the lower chamber. The results of the assay are presented in FIG. 7B. Both Vitaxin and the parental antibody LM609 yielded essentially identical inhibitory results. Specifically, Vitaxin and LM609 inhibited about 60% of the vitronectin-induced migration of endothelial cells compared to the $IgG_1$ control and to a sample with no inhibitor.

EXAMPLE IV

Vitaxin-Mediated Inhibition of $\alpha_v\beta_3$, In Animal Models

This Example describes the inhibition of tumor growth by Vitaxin in two animal models. Tumor growth was inhibited by inhibiting at least $\alpha_v\beta_3$-mediated neovascularization with Vitaxin.

The first model measures angiogenesis in the chick chorioallantoic membrane (CAM). This assay is a well recognized model for in vivo angiogenesis because the neovascularization of whole tissue is occurring. Specifically, the assay measures growth factor induced angiogenesis of chicken CAM vessels growing toward the growth factor-impregnated filter disk or into the tissue grown on the CAM. Inhibition of neovascularization is based on the amount and extent of new vessel growth or on the growth inhibition of tissue on the CAM. The assay has been described in detail by others and has been used to measure neovascularization as well as the neovascularization of tumor tissue (Ausprunk et al., *Am. J. Pathol.*, 79:597-618 (1975); Ossonski et al. *Cancer Res.*, 40:2300-2309 (1980); Brooks et al. *Science*, 264:569-571 (1994a) and Brooks et al. *Cell*, 79:1157-1164 (1994b).

Briefly, for growth factor induced angiogenesis filter disks are punched from #1 Whatman Qualitative Circles using a skin biopsy punch. Disks are first sterilized by exposure to UV light and then saturated with varying concentrations of TNF-α or HBSS as a negative control (for at least 1 hour) under sterile conditions. Angiogenesis is induced by placing the saturated filter disks on the CAMs.

Inhibition of angiogenesis is performed by treating the embryos with various amounts of Vitaxin and controls (antibody or purified human $IgG_1$). The treatments are performed by intravenous injection approximately 24 hours after disk placement. After 48 hours, CAMs are dissected and angiogenesis is scored on a scale of 1-4. HBSS saturated filter disks are used as the negative control, representing angiogenesis that may occur in response to tissue injury in preparing CAMs, and, values for these CAMS are subtracted out as background. Purified human $IgG_1$ is used as the negative control for injections since Vitaxin is of the human $IgG_1$ subclass. Vitaxin was found to inhibit TNF-α induced angiogenesis in a dose dependent manner. Maximal inhibition occurred with a single dose of Vitaxin at 300 µg which resulted in greater than 80% inhibition compared to the human $IgG_1$ control.

In addition to the above described CAM assay using growth factor-induced neovascularization, additional studies were performed utilizing tumor-induced neovascularization. For these assays, angiogenesis was induced by transplantating of $\alpha_v\beta_3$-negative tumor fragments into the CAMs. The use of $\alpha_v\beta_3$-negative tumor fragments ensures that any inhibition of tumor growth is due to the inhibition of $\alpha_v\beta_3$-mediated neovascularization by CAM-derived endothelial cells and not to adhesion events mediated by $\alpha_v\beta_3$ present on the tumor cells.

Inhibition of tumor growth was assessed by placing a single cell suspension of FG ($8\times10^6$ cells, pancreatic carcinoma) and HEp-3 cells ($5\times10^5$ cells, laryngeal carcinoma) onto CAMs in 30 µl. One week later, tumors are removed and cut into approximately 50 mg fragments at which time they are placed onto new CAMs. After 24 hours of this second placement embryos are injected intravenously with Vitaxin or human $IgG_1$ as a negative control. The tumors are allowed to grow for about 7 days following which they are removed and weighed.

Figure 6A:
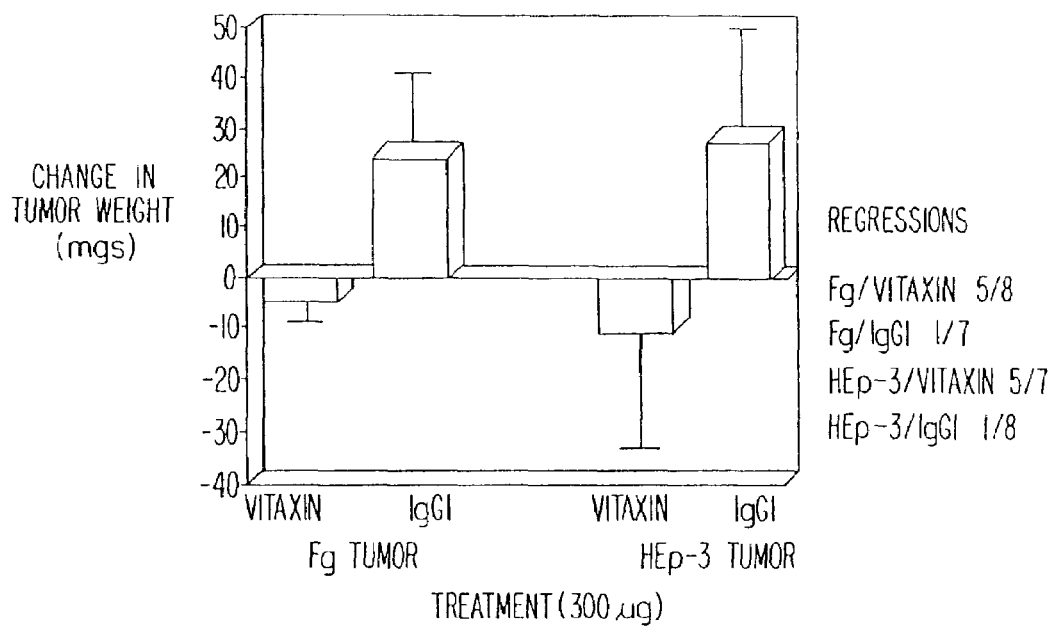
FIG. 6A shows the inhibition of the $\alpha v\beta 3$-negative Fg and HEp-3 human tumor fragments grown on chick chorioallantoic membranes (CAMs) following Vitaxin treatment.

The results of Vitaxin treatment on the neovascularization of tumors is shown in FIG. 6A. The data is expressed as a mean change in tumor weight and demonstrate that Vitaxin is able to inhibit the growth of $\alpha_v\beta_3$-negative tumors such as FG and HEp-3 tumor fragments. More specifically, there was a mean weight change for Vitaxin treated FG tumor fragments of −5.38 whereas a change of −11.0 was observed for Vitaxin treated HEp-3 tumors. The $IgG_1$ controls exhibited positive mean weight changes of 25.29 and 28.5 for the FG and HEp-3 tumor fragments, respectively. These results were obtained following a single intravenous injection.

In a second animal model, the inhibition of Vx2 carcinoma cells in rabbits was used as a measure of Vitaxin's inhibitory effect on tumors. The Vx2 carcinoma is a transplantable carcinoma derived from a Shope virus-induced papilloma. It was first described in 1940 and has since been used extensively in studies on tumor invasion, tumor-host interactions and angiogenesis. The Vx2 carcinoma is fibrotic in nature, highly aggressive, and exhibits features of an anaplastic type carcinoma. Propagation of Vx2 tumor is accomplished through serial transplantation in donor rabbits. Following subcutaneous transplantation, it has been reported that after an initial inflammatory reaction, host repair mechanisms set in between days 2 and 4. This repair mechanism is characterized by the formation of new connective tissue and the production of new capillaries. The newly formed capillaries are restricted to the repair zone at day 4, however, by day 8 they have extended to the outer region of the tumor. These characteristics and the pharmacokinetics of Vitaxin in rabbits were used to determine initial doses and scheduling of treatments for these experiments. The elimination half life of Vitaxin in animal serum dosed at 1, 5, and 10 mg/kg was found to be 38.9, 60.3, and 52.1 hours, respectively.

Growth of Vx2 tumors in the above animal model was used to study the effect of Vitaxin after early administration on primary tumor growth in rabbits implanted subcutaneously with Vx2 carcinoma. Briefly, Vx2 tumors (50 mg) were transplanted into the inner thigh of rabbits through an incision between the skin and muscle. Measurements of the primary tumor were taken throughout the experiment through day 25. At day 28 after the transplantation animals were sacrificed and tumors were excised and weighed. By day 28, tumors became extremely irregular in shape and as a result, measurements became difficult and were not reflective of tumor volume. Therefore measurements were assessed only through day 25.

In a first study, rabbits were treated starting at day 1 post tumor implantation with 5 and 1 mg/kg Vitaxin every four days for 28 days for a total of 7 doses). In both groups, inhibition of tumor growth was observed. In a second series of studies, rabbits were treated beginning at day 7 post tumor implantation as described above for a total of 5 doses. Inhibition of tumor growth was also observed.

It should be noted that administering a grafted antibody as a repeat dose treatment to rabbits might generate an immune response that can have a neutralizing effect on Vitaxin thus potentially comprising efficacy. Preliminary data suggest that approximately 25-50% of the animals develop such a response.

Figure 6B:
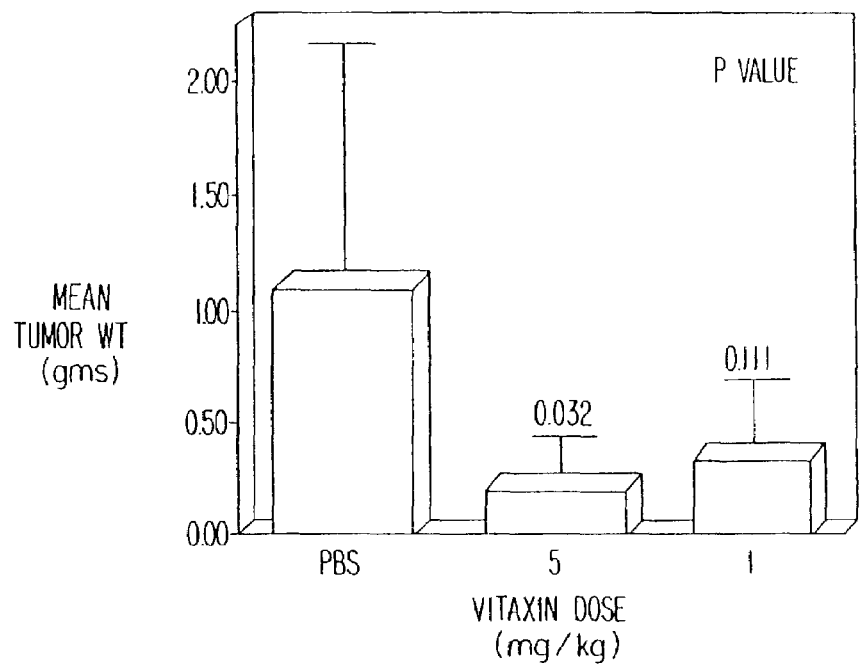
FIG. 6B shows the growth inhibition of Vx2 carcinomas implanted subcutaneously in rabbits at two different Vitaxin doses administered 1 day post implantation.
Figure 6C:
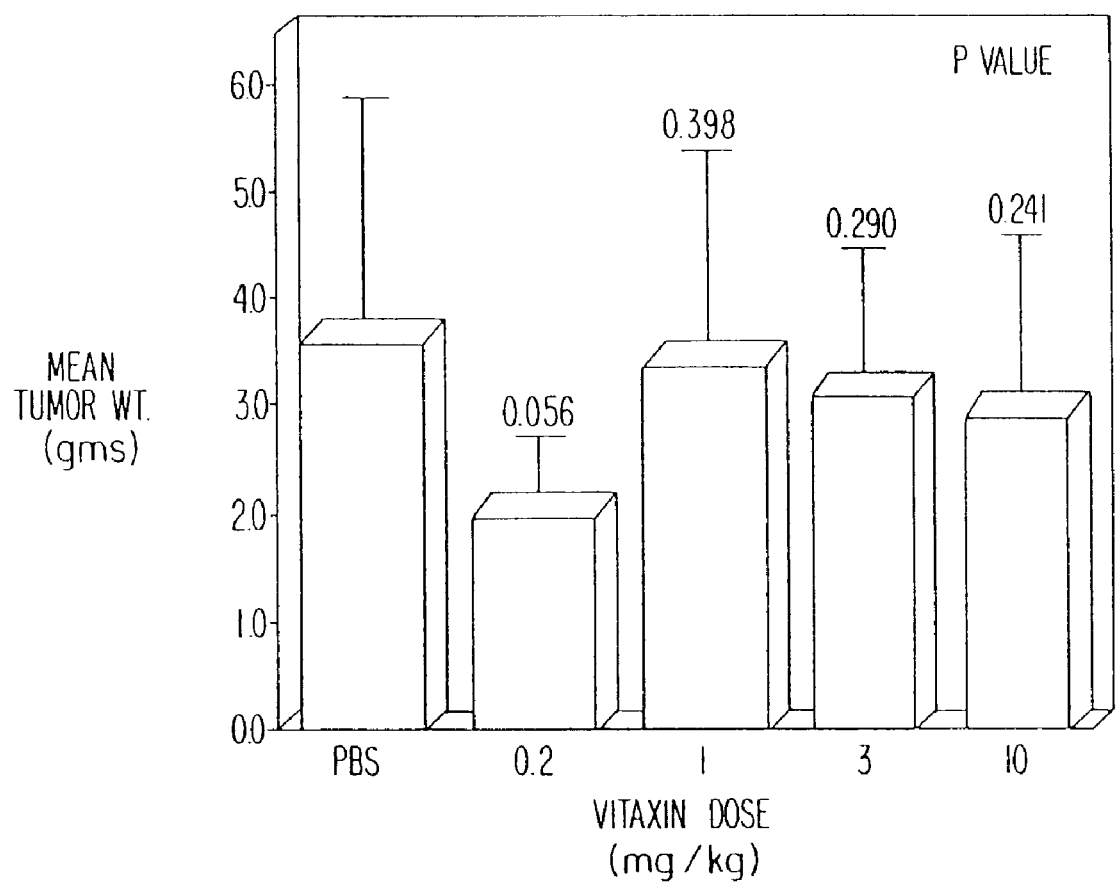
FIG. 6C similarly shows Vx2 tumor growth inhibition as in FIG. 6B, except that four different Vitaxin doses were administered beginning at 7 days post implantation.

The results of each of the Vitaxin treatments described above is shown in FIGS. 6B and 6C. In the rabbits receiving treatments on day 1, inhibition of tumor growth was observed in both the 1 mg/kg and the 5 mg/kg dosing groups compared to the control PBS treated control. Specifically, a growth inhibition of about 67 and 80% was observed, respectively, as measured by the mean tumor weight. A lesser degree of inhibition was observed in animals that began Vitaxin treatment on day 7 post implantation. These results are shown in FIG. 6C. In all cases, inhibition of tumor growth was not see at Vitaxin concentrations lower than 0.2 mg/kg.

EXAMPLE V

Construction of LM609 Grafted Functional Antibody Fragments

This Example shows the construction of functional LM609 grafted antibody fragments in which only the CDRs have been transferred from the LM609 donor antibody to a human acceptor framework.

CDR grafting of LM609 to produce a functional antibody fragment was accomplished by the methods set forth below. These procedures are applicable for the CDR grafting of essentially any donor antibody where amino acid residues outside of the CDRs from the donor antibody are not desired in the final grafted product.

Briefly, the protein sequence of the LM609 antibody, was determined by cloning and sequencing the cDNA that encodes the variable regions of the heavy and light chains as described in Example I. The CDRs from the LM609 donor antibody were identified and grafted into homologous human variable regions of a human acceptor framework. Identification of CDR regions were based on the combination of definitions published by Kabat et al., and MacCallum et al.

The boundaries of the CDR regions have been cumulatively defined by the above two publications and are residues 30-35, 47-66 and 97-106 for CDRs 1, 2 and 3, respectively, of the heavy chain variable region and residues 24-36, 46-56, and 89-97 for CDRs 1, 2 and 3, respectively, of the light chain variable region. Non-identical donor residues within these boundaries but outside of CDRs as defined by Kabat et al. were identified and were not substituted into the acceptor framework. Instead, functional non-donor amino acid residues were identified and substituted for certain of these non-identical residues.

As described below, the only non-identical residue outside of the CDRs as defined by Kabat et al. but within the CDRs as defined above is at position 49 of the LM609 light chain. To identify functional non-donor amino acids at this position, a library of nineteen antibodies was constructed that contained all non-donor amino acids at position 49 and then screened for binding activity against $\alpha_v\beta_3$.

Human immunoglobulin sequences were identified from the Brook-haven Protein Data Bank-Kabat Sequences of Proteins of Immunological Interest database (release 5.0). Human framework sequences showing significant identity to the murine LM609 variable region gene sequences were selected for receiving the LM609 CDRs. Human heavy chain variable region M72 'CL had 88% identity to frameworks 1, 2 and 3 of LM609 heavy chain and human light chain V region LS1 'CL had 79% identity to frameworks 1, 2 and 3 of LM609 light chain. With the exclusion of non-identical residues outside of the CDRs as defined by Kabat et al. murine LM609 CDR sequences as defined by Kabat et al. and MacCallum et al. were grafted onto the human frameworks. Using this grafting scheme, the final grafted product does not contain any amino acid residues outside of the CDRs as defined by Kabat et al. which are identical to an LM609 amino acid at the corresponding position (outside of residues: 31-35, 50-66 and 99-106 for CDRs 1, 2 and 3, respectively, of the heavy chain variable region and residues 24-34, 50-56, and 89-97 for CDRs 1, 2 and 3, respectively, of the light chain variable region). Moreover, no intermediates are produced which contain an amino acid residue outside of the CDRs as defined by Kabat et al. which are identical to the LM609 amino acid at that position. The CDR grafting procedures are set forth below.

Full-length CDR grafted variable region genes were synthesized by PCR using long overlapping oligonucleotides as described previously in Example II. The heavy chain variable region oligonucleotides were those described previously as SEQ ID NOS:9-13. The light chain variable region oligonucleotides were synthesized so as to contain the CDR grafted variable region as well as a stop codon at position 49. The five oligonucleotides for the light chain LM609 grafted variable region are show as SEQ ID NOS:23-27 where the second oligonucleotide in the series contains the stop codon at position 49 (SEQ ID NO:24).

All long oligonucleotides were gel purified. CDR grafting of the LM609 heavy chain variable region was constructed by mixing 5 overlapping oligonucleotides (SEQ ID NOS:9-13), at equimolar concentrations, in the presence of annealing PCR primers containing at least 18 nucleotide residues complementary to vector sequences for the efficient annealing of the amplified V region product to the single-stranded vector. The annealed mixture was fully converted to a double-stranded molecule with T4 DNA polymerase plus dNTPs and ligated with T4 ligase. The mutagenesis reaction (1 µl) was electroporated into E. coli strain DH10B (BRL), titered onto a lawn of XL-1 (Stratagene, Inc.) and incubated until plaques formed. Replica filter lifts were prepared and plaques containing $V_H$ gene sequences were screened either by hybridization with a digoxigenin-labeled oligonucleotide complementary to LM609 heavy chain CDR 2 sequences or reactivity with 7F11-alkaline phosphatase conjugate, a monoclonal antibody raised against the decapeptide sequence Tyr Pro Tyr Asp Val Pro Asp Tyr Ala Ser (SEQ ID NO:28) appended to the carboxy terminus of the vector $CH_1$ domain (Biosite, Inc., San Diego, Calif.).

Fifty clones that were double-positive were pooled and used to prepare uridinylated template for hybridization mutagenesis with the amplified CDR grafted LM609 $V_L$ product constructed in a similar fashion using the five overlapping oligonucleotides shown as SEQ ID NOS:23-27. The mutagenesis reaction was electroporated into E. coli strain DH10B. Randomly picked clones were sequenced to identify a properly constructed template for construction of the non-donor library at position 49. This template was prepared as a uridinylated template and an oligonucleotide population of the following sequence was used for site directed mutagenesis.

GGGAACGATA-19aa-GATGAGAAGC

The sequence 19aa in the above primer (SEQ ID NO:30) represents the fact that this primer specifies a sequence population consisting of 19 different codon sequences that encode each of the 19 non-donor amino acids. These amino acids are those not found at position 49 of LM609 and include all amino acids except for Lys. Clones that resulted from this mutagenesis were picked and antibody expressed by these clones were prepared. These samples were then screened for binding to $\alpha_v\beta_3$ in an ELISA assay. Clones having either Arg or Met amino acids in position 49 were functionally identified. The nucleotide and amino acid sequence of the LM609 grafted heavy chain variable region is show in FIG. 1A (SEQ ID NOS:1 and 2, respectively). The nucleotide and amino acid sequence of the LM609 grafted light chain variable region is shown in FIG. 7 (SEQ ID NOS:31 and 32, respectively).

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of inhibiting a function of $\alpha_v\beta_3$, comprising contacting $\alpha_v\beta_3$ with an antibody, or a functional fragment thereof, comprising at least one heavy chain polypeptide comprising a variable region amino acid sequence as that shown in FIG. 1A (SEQ ID NO:2) and at least one light chain polypeptide comprising a variable region amino acid sequence as that shown in FIG. 1B (SEQ ID NO:4) or a functional fragment thereof, said antibody or functional fragment thereof having integrin $\alpha_v\beta_3$ binding activity, integrin $\alpha_v\beta_3$ binding specificity or integrin $\alpha_v\beta_3$-inhibitory activity.

2. The method of claim 1, wherein said functional fragment is Fv.

3. The method of claim 1, wherein said functional fragment is Fab.

4. The method of claim 1, wherein said functional fragment is F(ab)$_2$.

5. The method of claim 1, wherein said functional fragment is scFV.

6. A method of treating diabetic retinopathy, neovascular glaucoma, macular degeneration, atherosclerosis, restenosis and osteoporosis, comprising contacting $\alpha_v\beta_3$ with an antibody, or a functional fragment thereof, comprising at least one heavy chain polypeptide comprising a variable region amino acid sequence as that shown in FIG. 1A (SEQ ID NO:2) and at least one light chain polypeptide comprising a variable region amino acid sequence as that shown in FIG. 1B (SEQ ID NO:4) or a functional fragment thereof, said antibody or functional fragment thereof having integrin $\alpha_v\beta_3$ binding activity, integrin $\alpha_v\beta_3$ binding specificity or integrin $\alpha_v\beta_3$-inhibitory activity.

7. The method of claim 6, wherein said functional fragment is Fv.

8. The method of claim 6, wherein said functional fragment is Fab.

9. The method of claim 6, wherein said functional fragment is F(ab)$_2$.

10. The method of claim 6, wherein said functional fragment is scFV.

11. A method of treating cancer, comprising contacting $\alpha_v\beta_3$ with an antibody, or a functional fragment thereof, comprising at least one heavy chain polypeptide comprising a variable region amino acid sequence as that shown in FIG. 1A (SEQ ID NO:2) and at least one light chain polypeptide comprising a variable region amino acid sequence as that shown in FIG. 1B (SEQ ID NO:4) or a functional fragment thereof, said antibody or functional fragment thereof having integrin $\alpha_v\beta_3$ binding activity, integrin $\alpha_v\beta_3$ binding specificity or integrin $\alpha_v\beta_3$-inhibitory activity.

12. The method of claim 11, wherein said cancer is selected from the group melanoma, glioblastoma, mammary carcinoma, angiofibroma, retrolental tumor, fibroplasia, hemangioma, and Kaposi's sarcoma.

13. The method of claim 11, wherein said cancer involves metastasis.

14. The method of claim 11, wherein said cancer involves a solid tumor.

15. The method of claim 11, wherein said functional fragment is Fv.

16. The method of claim 11, wherein said functional fragment is Fab.

17. The method of claim 11, wherein said functional fragment is F(ab)$_2$.

18. The method of claim 11, wherein said functional fragment is scFV.

19. A method of treating a tumor expressing $\alpha_v\beta_3$, comprising contacting $\alpha_v\beta_3$ with an antibody, or a functional fragment thereof, comprising at least one heavy chain polypeptide comprising a variable region amino acid sequence as that shown in FIG. 1A (SEQ ID NO:2) and at least one light chain polypeptide comprising a variable region amino acid sequence as that shown in FIG. 1B (SEQ ID NO:4) or a functional fragment thereof, said antibody or functional fragment thereof having integrin $\alpha_v\beta_3$ binding activity, integrin $\alpha_v\beta_3$ binding specificity or integrin $\alpha_v\beta_3$-inhibitory activity.

20. The method of claim 19, wherein said functional fragment is Fv.

21. The method of claim 19, wherein said functional fragment is Fab.

22. The method of claim 19, wherein said functional fragment is F(ab)$_2$.

23. The method of claim 19, wherein said functional fragment is scFV.

24. A method of treating an inflammatory disorder, comprising contacting $\alpha_v\beta_3$ with an antibody, or a functional fragment thereof, comprising at least one heavy chain polypeptide comprising a variable region amino acid sequence as that shown in FIG. 1A (SEQ ID NO:2) and at least one light chain polypeptide comprising a variable region amino acid sequence as that shown in FIG. 1B (SEQ ID NO:4) or a functional fragment thereof, said antibody or functional fragment thereof having integrin $\alpha_v\beta_3$ binding activity, integrin $\alpha_v\beta_3$ binding specificity or integrin $\alpha_v\beta_3$-inhibitory activity.

25. The method of claim 24, wherein said inflammatory disorder is rheumatoid arthritis or psoriasis.

26. The method of claim 24, wherein said functional fragment is Fv.

27. The method of claim 24, wherein said functional fragment is Fab.

28. The method of claim 24, wherein said functional fragment is F(ab)$_2$.

29. The method of claim 24, wherein said functional fragment is scFV.

30. A method of treating a pathological condition involving neovascularization, comprising contacting $\alpha_v\beta_3$ with an antibody, or a functional fragment thereof, comprising at least one heavy chain polypeptide comprising a variable region amino acid sequence as that shown in FIG. 1A (SEQ ID NO:2) and at least one light chain polypeptide comprising a variable region amino acid sequence as that shown in FIG. 1B (SEQ ID NO:4) or a functional fragment thereof, said antibody or functional fragment thereof having integrin $\alpha_v\beta_3$ binding activity, integrin $\alpha_v\beta_3$ binding specificity or integrin $\alpha_v\beta_3$-inhibitory activity.

31. The method of claim 30, wherein said functional fragment is Fv.

32. The method of claim 30, wherein said functional fragment is Fab.

33. The method of claim 30, wherein said functional fragment is F(ab)$_2$.

34. The method of claim 30, wherein said functional fragment is scFV.

* * * * *